US012745962B1

(12) United States Patent
Landry et al.

(10) Patent No.: US 12,745,962 B1
(45) Date of Patent: Sep. 29, 2026

(54) SYSTEMS AND METHODS FOR MANUFACTURING NEEDLE ARRAY ELECTRODES

(71) Applicant: PARADROMICS, INC., Austin, TX (US)

(72) Inventors: Michael Landry, Austin, TX (US); Yifan Kong, Menlo Park, CA (US); Kunal Sahasrabuddhe, Austin, TX (US); Kevin Boergens, Chicago, IL (US); Kim Reid, Austin, TX (US); Aleksandar Tadić, Austin, TX (US); Kimiko Nakajima, Austin, TX (US); Bryan Kerr, Austin, TX (US); Matthew Angle, Austin, TX (US)

(73) Assignee: Paradromics, Inc., Austin, TX (US)

( * ) Notice: Subject to any disclaimer, the term of this patent is extended or adjusted under 35 U.S.C. 154(b) by 611 days.

(21) Appl. No.: 18/177,024

(22) Filed: Mar. 1, 2023

Related U.S. Application Data

(60) Provisional application No. 63/315,689, filed on Mar. 2, 2022.

(51) Int. Cl.
*A61B 5/00* (2006.01)

(52) U.S. Cl.
CPC ...... *A61B 5/6868* (2013.01); *A61B 2562/066* (2013.01); *A61B 2562/125* (2013.01)

(58) Field of Classification Search
CPC ............ A61B 5/6868; A61B 2562/066; A61B 2562/125
See application file for complete search history.

(56) References Cited

U.S. PATENT DOCUMENTS

| | | | |
|---|---|---|---|
| 3,982,529 | A | 9/1976 | Sato |
| 5,008,733 | A | 4/1991 | Mine et al. |

(Continued)

FOREIGN PATENT DOCUMENTS

| | | | |
|---|---|---|---|
| EP | 2495011 A1 | 9/2012 | |
| WO | WO-2011139777 A2 | 11/2011 | |

(Continued)

OTHER PUBLICATIONS

Fofonoff et. al., Microelectrode Array Fabrication by Electrical Discharge Machining and Chemical Etching, IEEE Trans. on Biomed Engg., vol. 51, 6, Jun. 2004, pp. 890-895 (Year: 2004).*

(Continued)

*Primary Examiner* — Thomas J Hong
*Assistant Examiner* — Jose K Abraham
(74) *Attorney, Agent, or Firm* — Wilson Sonsini Goodrich & Rosati

(57) ABSTRACT

The present disclosure provides various embodiments of arrays and methods for manufacturing arrays. In one aspect, the present disclosure provides a method for manufacturing arrays. The method may comprise (a) processing a source material to form a plurality of elongated features; (b) depositing one or more films on a surface portion of the elongated features; (c) forming one or more electrical interconnections between (i) the elongated features and (ii) one or more active electronic components for processing one or more signals that are transmitted or received by or through the elongated features; (d) creating a needle array from the plurality of elongated features; and (e) dicing said needle array to form an array comprising a plurality of discrete electrodes. The one or more films may be configured to modify a property of the surface portion of the elongated features to enable or facilitate the one or more electrical interconnections.

23 Claims, 28 Drawing Sheets

(56) References Cited

U.S. PATENT DOCUMENTS 5,721,450 A 2/1998 Miles
5,814,122 A 9/1998 Huang
6,049,038 A 4/2000 Suzuki
6,156,978 A 12/2000 Peck et al.
6,249,965 B1 6/2001 Bullara et al.
6,393,327 B1 5/2002 Scribner
6,511,463 B1 * 1/2003 Wood ............... A61B 5/150022 216/75
6,647,297 B2 11/2003 Scribner et al.
6,815,258 B2 11/2004 Vincent
6,920,359 B2 7/2005 Meadows et al.
6,940,182 B2 9/2005 Hilton et al.
7,091,060 B2 8/2006 Bolken et al.
7,134,198 B2 11/2006 Nakatani et al.
7,306,976 B2 * 12/2007 Feustel ................. H01L 23/295 257/E21.503
7,991,475 B1 8/2011 Tang et al.
8,010,208 B2 8/2011 Nimer et al.
8,024,049 B1 9/2011 Gilson et al.
8,280,516 B2 10/2012 Graupe
8,406,889 B2 3/2013 Llinas et al.
8,412,332 B2 4/2013 Massoud-Ansari et al.
8,649,873 B2 2/2014 Moffitt et al.
8,798,737 B2 8/2014 Merz et al.
8,805,530 B2 8/2014 John
8,849,408 B1 9/2014 Gilson et al.
8,929,992 B2 1/2015 Toader et al.
8,944,985 B2 2/2015 Bonmassar et al.
8,991,680 B1 3/2015 Schulman et al.
10,327,655 B2 6/2019 Angle et al.
10,390,724 B2 8/2019 Fonash et al.
10,799,132 B2 * 10/2020 Negi ...................... A61B 5/294
11,395,924 B2 7/2022 McLaughlin et al.
11,401,620 B2 8/2022 Kong et al.
12,171,995 B1 12/2024 Reid et al.
2002/0014688 A1 2/2002 Ramalingam et al.
2003/0100823 A1 5/2003 Kipke et al.
2004/0006264 A1 1/2004 Mojarradi et al.
2004/0026792 A1 2/2004 Vincent
2004/0034368 A1 2/2004 Pless et al.
2004/0119169 A1 6/2004 Hanawa
2004/0133118 A1 7/2004 Llinas
2004/0222010 A1 11/2004 Tonucci et al.
2005/0217796 A1 10/2005 Carter et al.
2005/0267347 A1 12/2005 Oster
2006/0172179 A1 8/2006 Gu et al.
2006/0206161 A1 9/2006 Nicolelis et al.
2006/0265039 A1 11/2006 Bartic et al.
2007/0106143 A1 5/2007 Flaherty
2007/0142872 A1 6/2007 Mickle et al.
2007/0169333 A1 * 7/2007 Donoghue ............... A61B 5/24 600/372
2007/0250142 A1 10/2007 Francis et al.
2008/0140159 A1 6/2008 Bornhoft et al.
2008/0170819 A1 7/2008 Kodama et al.
2008/0205829 A1 8/2008 Jacobsen et al.
2008/0208283 A1 8/2008 Vetter et al.
2009/0004471 A1 1/2009 Amthor
2009/0069706 A1 3/2009 Boogaard et al.
2009/0120216 A1 5/2009 Chiou et al.
2009/0301994 A1 * 12/2009 Bhandari ............... A61B 5/685 216/11
2009/0304774 A1 12/2009 Liang et al.
2010/0016928 A1 1/2010 Zdeblick et al.
2010/0029148 A1 2/2010 Perlin et al.
2010/0069776 A1 3/2010 Greger et al.
2010/0114272 A1 5/2010 Haidarliu et al.
2010/0133697 A1 6/2010 Nilsson
2010/0161019 A1 6/2010 Clark et al.
2011/0208031 A1 8/2011 Wolfe et al.
2012/0041294 A1 2/2012 Bai
2012/0109262 A1 5/2012 Martens et al.
2012/0279852 A1 11/2012 Zach
2012/0310230 A1 12/2012 Willis
2013/0030274 A1 1/2013 Jamieson et al.
2013/0030500 A1 1/2013 Toader et al.
2013/0072808 A1 3/2013 Neves et al.
2013/0175733 A1 7/2013 De et al.
2013/0190586 A1 7/2013 Akingba et al.
2013/0190851 A1 7/2013 Schouenborg et al.
2013/0204317 A1 8/2013 Sauter-Starace et al.
2013/0274843 A1 10/2013 Barker et al.
2013/0337583 A1 12/2013 Kobayashi et al.
2014/0094674 A1 4/2014 Nurmikko et al.
2014/0107728 A1 4/2014 Fried et al.
2014/0161973 A1 6/2014 Tang et al.
2014/0309548 A1 10/2014 Merz et al.
2014/0330354 A1 11/2014 Shelton et al.
2014/0350634 A1 11/2014 Grill et al.
2015/0005573 A1 1/2015 Lehmann et al.
2015/0065831 A1 3/2015 Popovic et al.
2015/0224299 A1 8/2015 Wahlstrand
2015/0305643 A1 10/2015 Negi et al.
2015/0368822 A1 12/2015 Sammelselg et al.
2016/0029998 A1 2/2016 Brister et al.
2016/0049293 A1 2/2016 Li et al.
2016/0074655 A1 3/2016 Mercanzini et al.
2016/0128588 A1 5/2016 Melosh et al.
2016/0235967 A1 8/2016 Shan et al.
2016/0302687 A1 10/2016 Lee et al.
2017/0007813 A1 1/2017 Negi et al.
2017/0157407 A1 6/2017 Zellmer et al.
2017/0165474 A1 6/2017 Karpman et al.
2017/0271919 A1 9/2017 Von Novak, III et al.
2017/0290521 A1 10/2017 Angle et al.
2017/0358488 A1 12/2017 Cho et al.
2018/0160929 A1 6/2018 Ashe et al.
2018/0169403 A1 6/2018 Park
2018/0221663 A1 8/2018 Saini
2018/0264191 A1 9/2018 Dagdeviren et al.
2018/0296243 A1 10/2018 Hanson et al.
2018/0345019 A1 12/2018 Greenberg et al.
2019/0076644 A1 3/2019 Olson
2019/0175902 A1 6/2019 Lee et al.
2019/0388678 A1 * 12/2019 Najafi ................... A61M 5/158
2020/0022601 A1 1/2020 Rogers et al.
2020/0077974 A1 3/2020 Avanaki et al.
2020/0206516 A1 7/2020 Zellmer et al.
2020/0215335 A1 * 7/2020 McLaughlin ............ A61N 1/05
2020/0315477 A1 10/2020 Constandinou et al.
2020/0393438 A1 12/2020 Wijdenes et al.
2021/0098341 A1 4/2021 Kong et al.
2021/0138249 A1 5/2021 Howard
2021/0170176 A1 6/2021 Martens et al.
2021/0198613 A1 * 7/2021 Curley ............... G01N 33/5014
2021/0310988 A1 10/2021 McGrath et al.
2021/0338158 A1 11/2021 Kendall et al.
2022/0175320 A1 6/2022 Shah et al.
2023/0120082 A1 4/2023 Hettick et al.
2023/0225728 A1 7/2023 List

FOREIGN PATENT DOCUMENTS

WO WO-2012141714 A1 10/2012
WO WO-2012170340 A2 12/2012
WO WO-2017127551 A1 7/2017
WO WO-2017180482 A1 10/2017
WO WO-2018055369 A1 3/2018
WO WO-2018183967 A1 10/2018
WO WO-2019089919 A2 5/2019
WO WO-2024086542 A1 4/2024

OTHER PUBLICATIONS

Liao et. al., Fabrication of high aspect ratio microstructure arrays by micro reverse wire-EDM, J. Micromech. Microeng. 15 (2005) 1547-1555. (Year: 2005).*

Applied Materials Brochure. Enabling Next Generation Electronic Medical Devices With Atomic Layer Deposition. 1-9. No date or author available.

Astaneh, et al. Atomic Layer Deposition on Dental Materials: Processing Conditions and Surface Functionalization to Improve

(56) References Cited

OTHER PUBLICATIONS

Physical, Chemical, and Clinical Properties—A Review. Acta Biomaterialia 121:103-118 (2021).
Blomberg, et al. Atomic Layer Deposition Coatings for Medical Devices. ECS Meeting Abstracts, vol. MA2019-02, G02-Atomic Layer Deposition Applications 15:1126, 1-4 (2019). (Abstract Only).
Co-pending U.S. Appl. No. 18/806,233, inventors Landry; Michael E. et al., filed Aug. 15, 2024.
Co-pending U.S. Appl. No. 18/934,011, inventors Angle; Matthew et al., filed Oct. 31, 2024.
Co-pending U.S. Appl. No. 19/179,904, inventors Matthew; R. Angle et al., filed Apr. 15, 2025.
Ghelich, et al. Unprotected Sidewalls of Implantable Silicon-based Neural Probes and Conformal Coating as a Solution. Npj Materials Degradation 5:1-16 (2021).
Goto, Kazuya. et al. Transcutaneous photocoupler for transmission of biological signals. Optics Letters 27(20):1797-1799 (2002).
Li, et al. Ultra-Long-Term Reliable Encapsulation Using an Atomic Layer Deposited HfO2/Al2O3/HfO2 Triple-Interlayer for Biomedical Implants. Coatings 9:579, 1-13 (2019).
PCT/US2023/077021 International Search Report and Written Opinion dated Feb. 22, 2024.
U.S. Appl. No. 17/031,584 Office Action dated Dec. 15, 2023.
U.S. Appl. No. 17/031,584 Office Action dated Feb. 11, 2025.
U.S. Appl. No. 17/031,584 Office Action dated May 17, 2024.
U.S. Appl. No. 17/856,843 Office Action dated Jun. 11, 2025.
U.S. Appl. No. 17/937,374 Notice of Allowance dated Nov. 5, 2024.
U.S. Appl. No. 17/937,374 Notice of Allowance dated Sep. 18, 2024.
U.S. Appl. No. 17/937,374 Office Action dated Jun. 12, 2024.
U.S. Appl. No. 17/937,374 Supplemental Notice of Allowability dated Nov. 18, 2024.
U.S. Appl. No. 18/316,127 Office Action dated Jul. 17, 2025.
Webb, James Luke et al. Detection of biological signals from a live mammalian muscle using an early stage diamond quantum sensor. Scientific Reports 11:2412, 1-11 (2021).
Angle et al. Neuronal Recordings with Solid-Conductor Intracellular Nanoelectrodes (SCINEs). PLOS One 7(8):E43194 (Aug. 2012). 8 pages.
Bashkatov et al. Optical Properties of the Subcutaneous Adipose Tissue in the Spectral Range 400-2500 nm. Optics and Spectroscopy, vol. 99, No. 5, 2005, pp. 836-842.
Bouton, C. et al., Restoring cortical control of functional movement in a human with quadriplegia. Nature (2016). 13 pages. Retrieved Feb. 15, 2023 at URL: https://www.researchgate.net/profile/Marcia-Bockbrader/publication/301247939_Restoring_cortical_control_of_functional_movement_in_a_human_with_quadriplegia/links/59d70c77a6fdcc52acaa0075/Restoring-cortical-control-of-functional-movement-in-a-human-with-quadriplegia.pdf.
Brenner, W. Use underfill encapsulants to enhance flip-chip assembly reliability. Electronic Design. Jul. 30, 2012; Retrieved Feb. 29, 2016 available at http://electronicdesign.com/boards/useunderfillencapsulantsenhanceflipchipassemblyreliability.
Co-pending U.S. Appl. No. 17/856,843, inventors Angle; Matthew et al., filed Jul. 1, 2022.
Co-pending U.S. Appl. No. 17/937,374, inventors Reid; Kimberly G. et al., filed Sep. 30, 2022.
Co-pending U.S. Appl. No. 18/053,106, inventors Angle; Matthew et al., filed Nov. 7, 2022.
Co-pending U.S. Appl. No. 18/184,572, inventors Burrows; James et al., filed Mar. 15, 2023.
Co-pending U.S. Appl. No. 18/316,127, inventor Burrows; James, filed May 11, 2023.
Co-pending U.S. Appl. No. 18/329,485, inventors Angle; Matthew et al., filed Jun. 5, 2023.
Co-pending U.S. Appl. No. 18/342,602, inventors Angle; Matthew et al., filed Jun. 27, 2023.
Hajjhassan et al. NeuroMEMS: Neural Probe Microtechnologies. Sensors 8(10):6704-6726 (Oct. 25, 2008). doi: https://doi.org/10.3390/s8106704.
Instruction for use (IFU) Blackrock research assemblies. Blackrock Microsystems, LLC. 2014. pp. 0-13.
International Search Report dated Jun. 19, 2017 for International Application No. PCT/US2017/026707.
Johnson, L.J. et al., A novel high electrode count spike recording array using an 81,920 pixel transimpedance amplifier-based imaging chip. Journal of Neuroscience methods. 205; 2012: 223-232.
Johnson, R. Wayne, Chapter 19: Flip Chip Assembly and underfilling, Auburn University (2001). Available at https://pdfs.semanticscholar.org/3c24/524ef9ede82c95ba10caae142e3ca8b58966.pdf.
Liao et al. Fabrication of high aspect ratio microstructure arrays by micro reverse wire-EDM. J. Micromech. Microeng. 15 (2005) 1547-1555.
Mauron, F. Improvements in glass encapsulation technology offer significant advantages for implantable medical devices. Valtronic. p. 1-10. Jul. 2013. Retrieved Mar. 2, 2023 at URL: http://www.implantable-device.com/wp-content/uploads/2013/07/Valtronic-Glass-Encapsulation-White-Paper.pdf.
Office Action dated Jun. 30, 2017 for U.S. Appl. No. 15/482,583.
Office Action dated Nov. 28, 2017 for U.S. Appl. No. 15/482,583.
PCT/US2018/025576 International Search Report and Written Opinion dated Jul. 30, 2018.
Scribner, D. et al., A retinal prosthesis technology based on CMOS microelectronics and microwire glass electrodes. IEEE transactions on biomedical circuits and systems, 1(1); Mar. 2007: p. 73-84.
Stolp et al. Immune responses at brain barriers and implications for brain development and neurological function in later life. Frontiers in Integrative Neuroscience, vol. 7, Article 61 (Aug. 23, 2013). 14 pages.
U.S. Appl. No. 15/482,583 Notice of Allowance dated Mar. 6, 2019.
U.S. Appl. No. 16/584,630 Notice of Allowance dated Apr. 27, 2022.
U.S. Appl. No. 16/584,630 Notice of Allowance dated May 26, 2022.
U.S. Appl. No. 15/482,583 Office Action dated Aug. 28, 2018.
U.S. Appl. No. 15/482,583 Notice of Allowance dated Apr. 23, 2019.
U.S. Appl. No. 15/482,583 Notice of Allowance dated Mar. 20, 2019.
U.S. Appl. No. 16/584,630 Office Action dated Mar. 1, 2022.
U.S. Appl. No. 17/031,584 Office Action dated Apr. 18, 2023.
U.S. Appl. No. 17/856,843 Office Action dated Feb. 24, 2026.
U.S. Appl. No. 18/053,106 Office Action dated Mar. 3, 2026.
U.S. Appl. No. 18/316,127 Office Action dated Mar. 4, 2026.
U.S. Appl. No. 18/342,602 Office Action dated Feb. 24, 2026.
U.S. Appl. No. 18/806,233 Office Action dated Jan. 14, 2026.
U.S. Appl. No. 17/031,584 Office Action dated Sep. 26, 2025.
U.S. Appl. No. 18/329,485 Office Action dated Nov. 26, 2025.
U.S. Appl. No. 17/031,584 Office Action dated Apr. 30, 2026.
U.S. Appl. No. 18/806,233 Notice of Allowance dated Apr. 24, 2026.

* cited by examiner

Details of Sparking Gap (Scott, 1991)

SYSTEMS AND METHODS FOR MANUFACTURING NEEDLE ARRAY ELECTRODES

CROSS-REFERENCE

This application claims the benefit of U.S. Provisional Application No. 63/315,689, filed Mar. 2, 2022, which is incorporated herein by reference in its entirety.

STATEMENT AS TO FEDERALLY SPONSORED RESEARCH AND DEVELOPMENT

This invention was made with Government support under Contract Number R44MH125700 awarded by National Institutes of Health. The government has certain rights in the invention.

BACKGROUND

There are many uses for electrode arrays in medical devices. These arrays can be adapted to pack a large number of electrodes into a given space. Such arrays can be utilized for neuroscience applications and implantable Brain Computer Interfaces (BCI).

SUMMARY

The present application provides systems and methods for manufacturing electrodes. In one aspect, the present disclosure provides a method for fabricating an array of electrodes. The method may comprise (a) processing a source material using an additive or subtractive operation to form a plurality of elongated features; (b) depositing one or more films on a surface portion of the plurality of elongated features; (c) forming one or more electrical interconnections between (i) the elongated features and (ii) one or more active electronic components for processing one or more signals that are transmitted or received by or through the elongated features, wherein the one or more films are configured to modify a property of the surface portion of the elongated features to enable or facilitate the one or more electrical interconnections; (d) creating a needle array from the plurality of elongated features; and (e) dicing said needle array to form an array comprising a plurality of discrete electrodes. In some embodiments, the needle array is formed by laser cutting, electrochemical machining, or mechanical dicing of the elongated features.

In some embodiments, the additive or subtractive operation comprises electrical discharge machining (EDM). In some embodiments, the electrical discharge machining comprises (i) wire EDM or (ii) sinker EDM.

In some embodiments, each discrete electrode of the plurality of discrete electrodes is configured to function as an independent electrode. In some embodiments, each discrete electrode of the array is electrically isolated from one or more other electrodes of the array. In some embodiments, the plurality of discrete electrodes are in communication with the one or more active electronic components to facilitate or enable signal transmission and processing. In some embodiments, one or more electrodes of the array are built or formed directly onto a hermetic feedthrough that is coupled to or integrated with a hermetic package comprising the one or more active electronic components. In some embodiments, the active electronic components are provided within the hermetic package.

In some embodiments, the one or more electrical interconnections comprise a ball bond or a stud bump. In some embodiments, the one or more electrical interconnections comprise an array of ball bonds or stud bumps. In some embodiments, the one or more films comprise a semitransparent film. In some embodiments, the one or more films comprise a layer of platinum and/or a layer of gold. In some embodiments, the one or more electrical interconnections comprise one or more bonds formed by depositing a ball comprising a conductive material on the one or more elongated features or the one or more films deposited thereon. In some embodiments, the one or more bonds comprise a thermocompression bond, a diffusion bond, a diffusion weld, or a thermosonic bond.

In some embodiments, the method may further comprise, prior to (c), providing a hermetic feedthrough comprising a plurality of vias for establishing or facilitating the one or more electrical interconnections between (i) the elongated features and (ii) the one or more active electronic components. In some embodiments, the method may further comprise depositing one or more thin films on an outside surface of the hermetic feedthrough, wherein the one or more thin films are configured to modify a property of the outside surface of the hermetic feedthrough to enable or facilitate the one or more electrical interconnections.

In some embodiments, the one or more electrical interconnections are formed by bonding the plurality of vias to the one or more elongated features. In some embodiments, the plurality of vias and the one or more elongated features are (i) aligned with each other or (ii) offset relative to each other. In some embodiments, the bonding of the plurality of vias and the one or more elongated features comprises forming one or more gold-to-gold diffusion bonds.

In some embodiments, the one or more electrical interconnections extend through one or more film stacks deposited on the feedthrough or the elongated features. In some embodiments, the one or more film stacks comprise (i) the one or more films deposited on the elongated features and/or (ii) the one or more thin films deposited on the feedthrough.

In some embodiments, the method may further comprise laser dicing the one or more thin films deposited on the outside surface of the hermetic feedthrough and/or the one or more films deposited on the plurality of elongated features to form the plurality of discrete electrodes. In some embodiments, the plurality of discrete electrodes are in electrical communication with a worktable and each other via the one or more films or the one or more thin films prior to said laser dicing of the one or more films. In some embodiments, the plurality of discrete electrodes are (i) physically separate from each other, (ii) electrically isolated, and (iii) conductive through the hermetic feedthrough subsequent to said laser dicing of the one or more films.

In some embodiments, the method may further comprise applying a coating before said dicing and thereafter removing recast material produced during said dicing. In some embodiments, the method may further comprise performing a cleaning operation before forming a bond or depositing a film. In some embodiments, the method may further comprise heat treating the array to improve diffusion across bonds and to relieve residual stress.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "real time" or "real-time," as used interchangeably herein, generally refers to an event (e.g., an operation, a process, a method, a technique, a computation, a calculation, an analysis, a visualization, an optimization, etc.) that is performed using recently obtained (e.g., collected or received) data. In some cases, a real time event may be performed almost immediately after an initial event or within a short enough time span after such initial event, such as within at most 1 second, 0.5 seconds, 0.1 seconds, 0.05 seconds, 0.01 seconds, 5 ms, 1 ms, 0.5 ms, 0.1 ms, 0.05 ms, 0.01 ms, 0.005 ms, 0.001 ms, 0.0005 ms, 0.0001 ms, or less.

Overview

One or more semiconductor manufacturing methods can be used to fabricate electrodes one layer at a time on very small scales. This type of "additive" approach is promising but not the only viable approach. Another approach is to manufacture arrays using subtractive machining methods such as Electrical Discharge Machining (EDM). This can be a viable technique for making parts at the necessary scale and tolerance.

Figure 1:
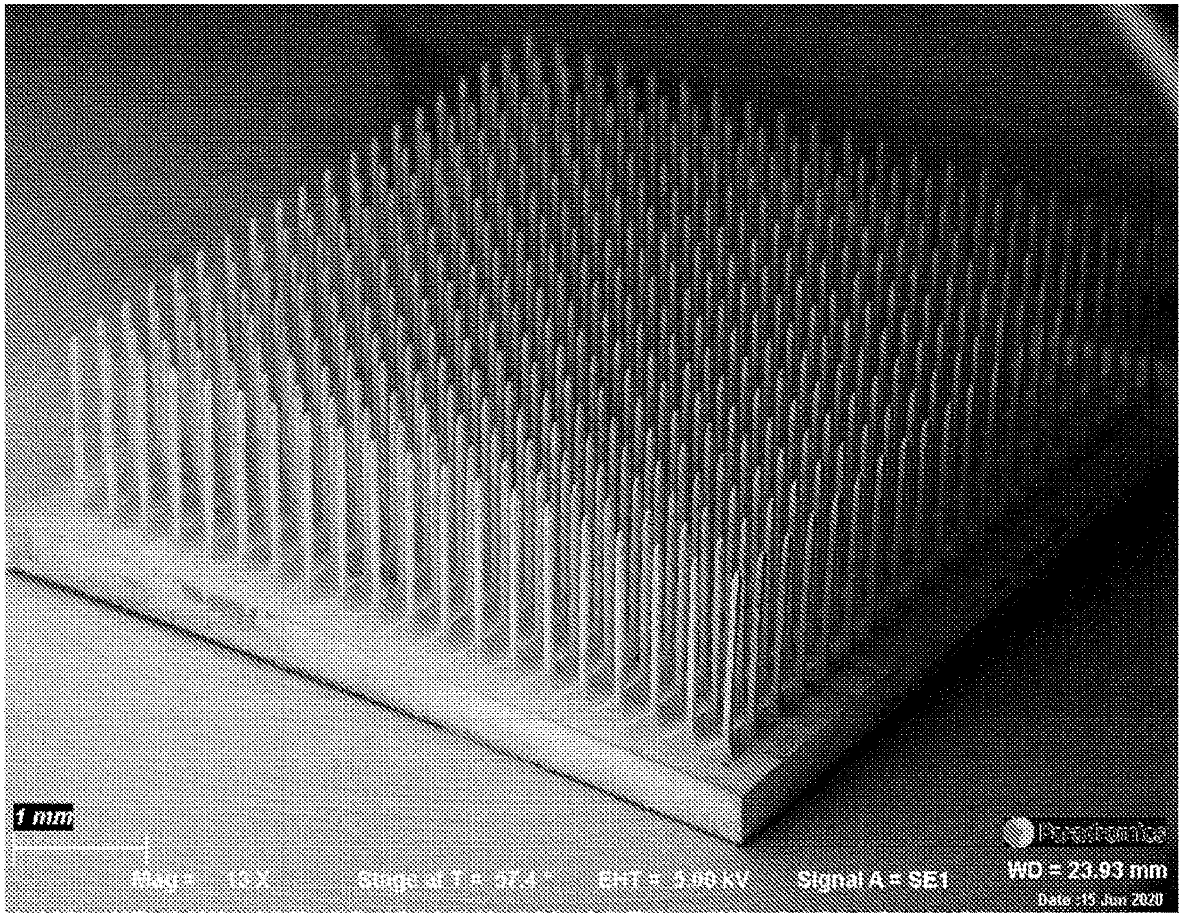
FIG. 1 schematically illustrates an array of needles, in accordance with some embodiments.

Micro needle arrays can be fabricated using EDM, but brain computer interfaces (BCIs) may utilize micro electrode arrays. They are very similar with one important distinction, their electrical connections. An array of needles made with EDM can be connected to each other as shown in FIG. 1. Since EDM can only be used to cut materials that are electrically conductive, each of these needles is electrically connected to all of the other needles in the array. This can be appropriate for some medical applications, but BCIs require each needle to function as an independent electrode for enhanced signal capture and transmission. Additionally, in any fully implantable version of a BCI, each electrode must be connected to active electronics for signal processing. These active electronics can be encased or housed in a hermetic package to protect them from the environment of the body. EDM can be used to manufacture needle arrays. However, because the "cutting" action of EDM is electrical in nature, electrically isolating the electrodes can destroy the array, since each electrode would fall away upon isolation.

The present disclosure resolves this issue and enables a process for building the electrodes directly onto a hermetic feedthrough. This can then be incorporated into a fully hermetic package for the active electronics. The process also produces a device that is biocompatible, biostable, and has the mechanical integrity required for implantation.

EDM

Micro needle/electrode arrays are useful in many applications, especially in medical devices used for drug delivery. Needles and/or electrodes can be manufactured in various ways including many additive and subtractive manufacturing technologies. One subtractive technology can cut electrodes from a source material (e.g., a solid metal block) using EDM. Two non-limiting examples of subtypes of EDM that could be used include wire EDM (WEDM) and sinker EDM.

Figure 2:
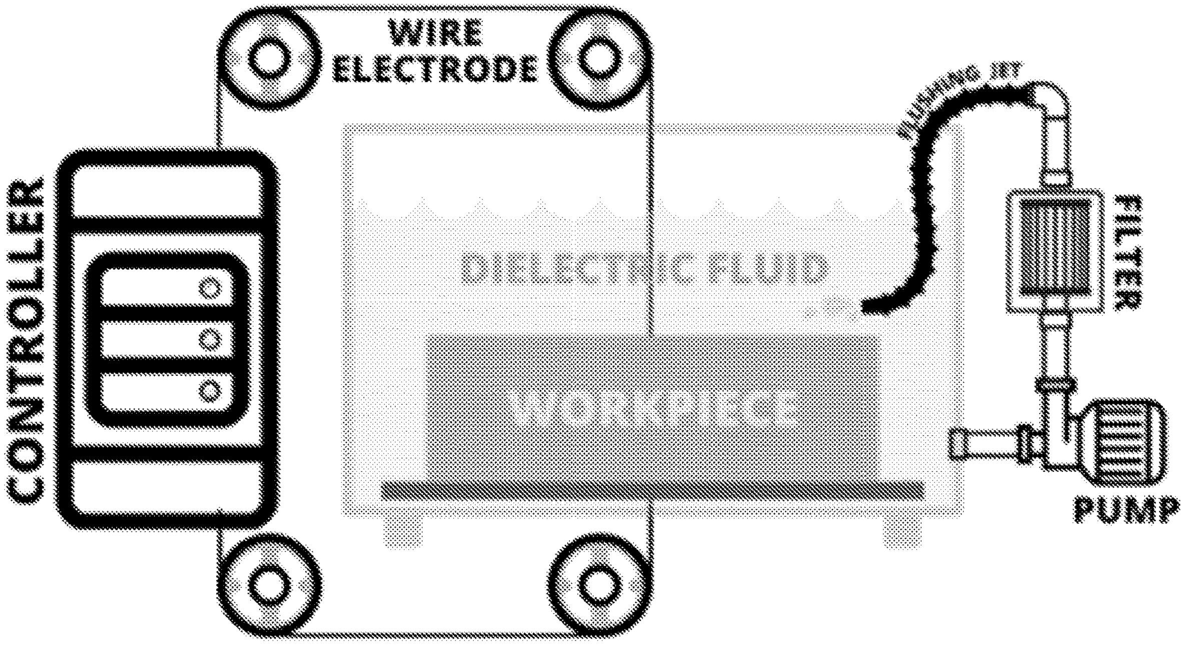
FIG. 2 schematically illustrates wire electrical discharge machining (EDM), in accordance with some embodiments.

The basics of WEDM are shown in FIG. 2. A workpiece can be provided on or clamped to a "machine table" as shown so that the two are electrically connected.

Figure 3:
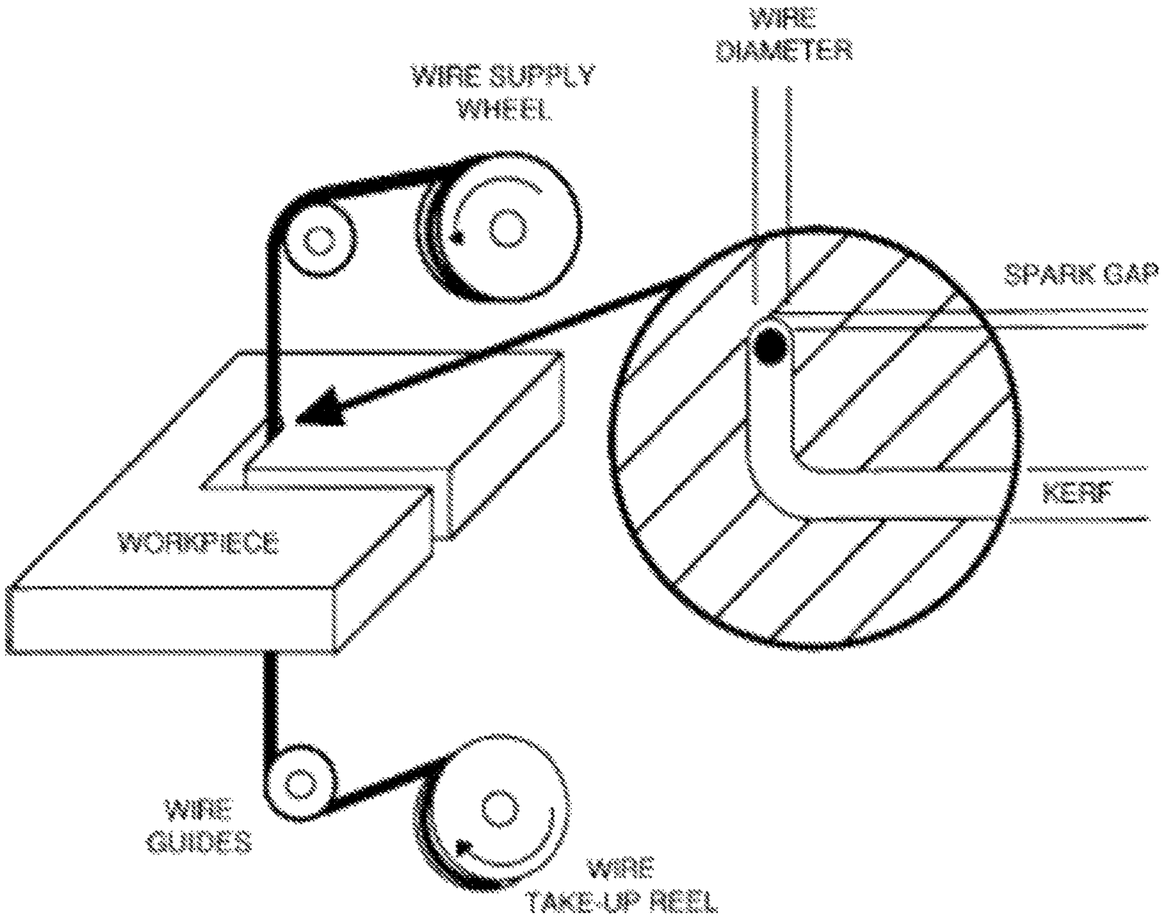
FIG. 3 schematically illustrates a cutting action that can be performed to shape or form an array, in accordance with some embodiments.
Figure 4:
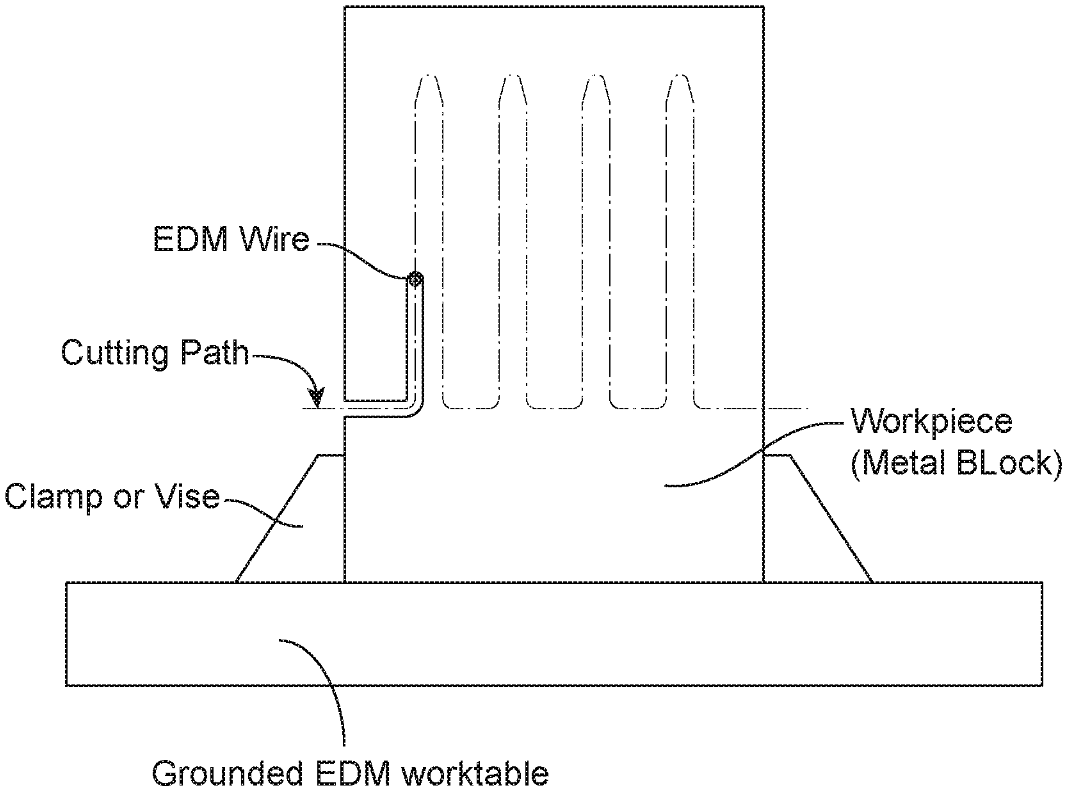
FIG. 4 schematically illustrates a cutting action that can be performed to shape or form an array, in accordance with some embodiments.
Figure 5:
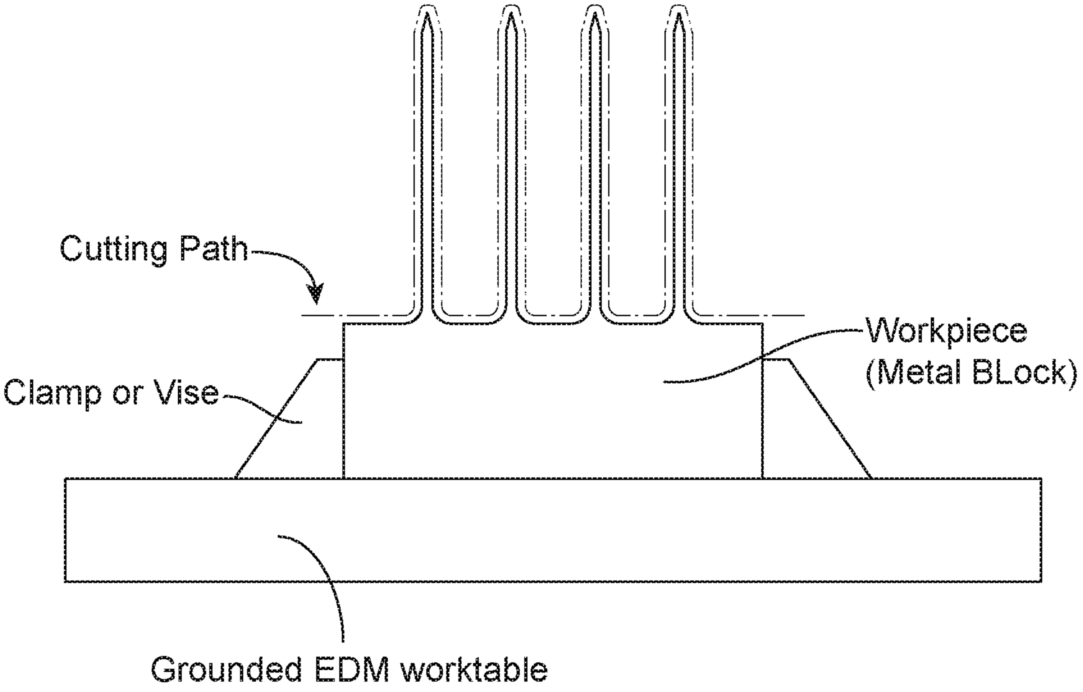
FIG. 5 schematically illustrates a cutting action that can be performed to shape or form an array, in accordance with some embodiments.

FIG. 3 and FIG. 4 shows the "cutting" action that can be performed to shape or form an array. This process is typically called "cutting" but it is more accurately described as an ablation caused by an electrical spark. A cutting path is programmed into the machine and the wire follows this path as it cuts the workpiece. Cutting is accomplished by an electric spark going from the wire, across a very small gap, into the workpiece, and then to ground via the EDM machine worktable. The spark ablates the surface of the workpiece closest to the wire. This electrical path is critical for EDM function. When the cut is complete as shown in FIG. 5, the excess material falls off as scrap and the final part is left behind.

Figure 6:
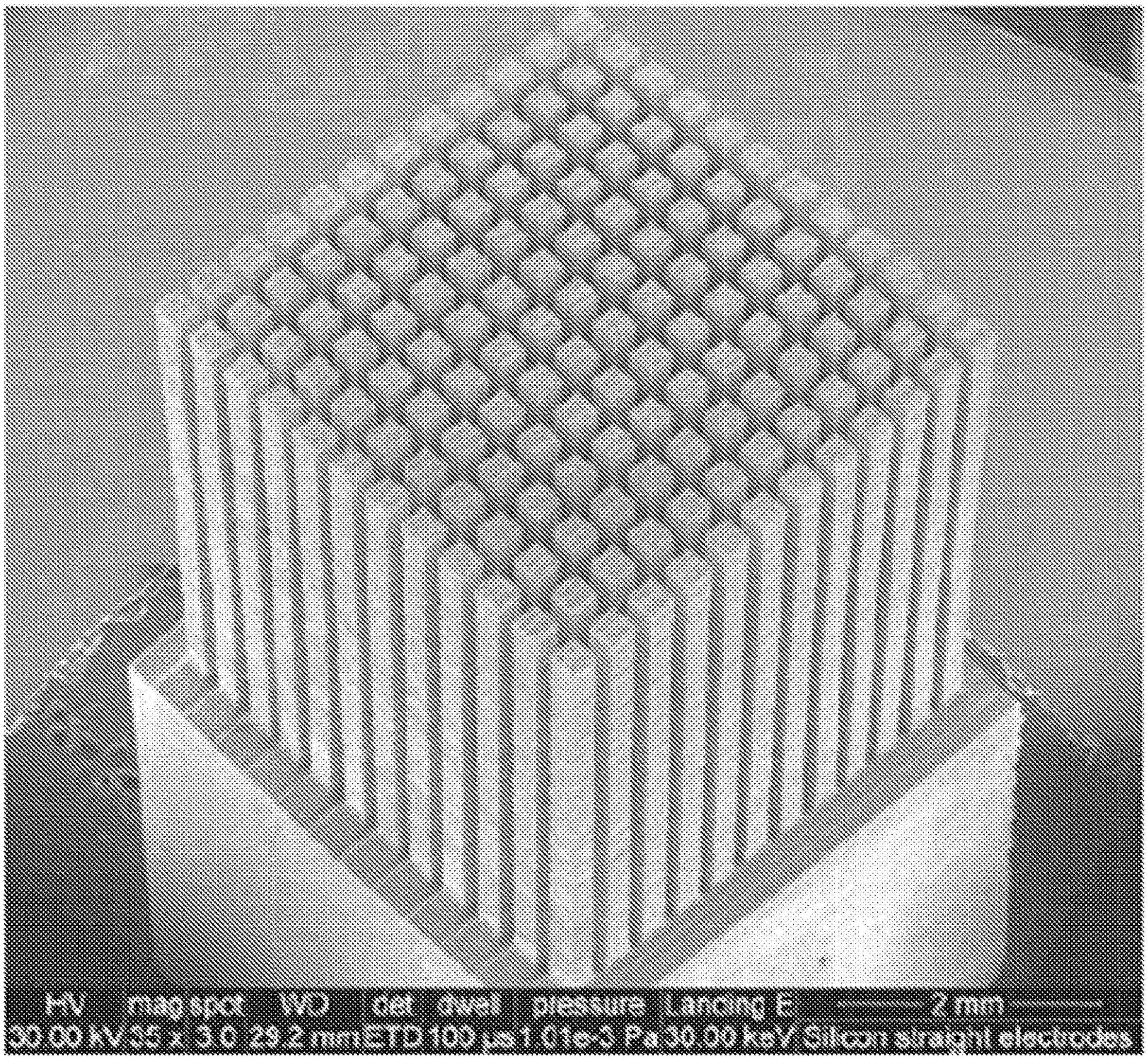
FIG. 6 schematically illustrates an array of needles that can be formed using wire EDM, in accordance with some embodiments.

A 2D array can be created by rotating the workpiece 90 degrees and repeating the same cut to make small needle arrays. FIG. 6 shows an example of a 12×12 needle array cut by WEDM. In this example, tips of these "needles" are blunt but can be further processed to form a sharp tip by adjusting the WEDM cutting paths.

Ball Bonding

Figure 7:
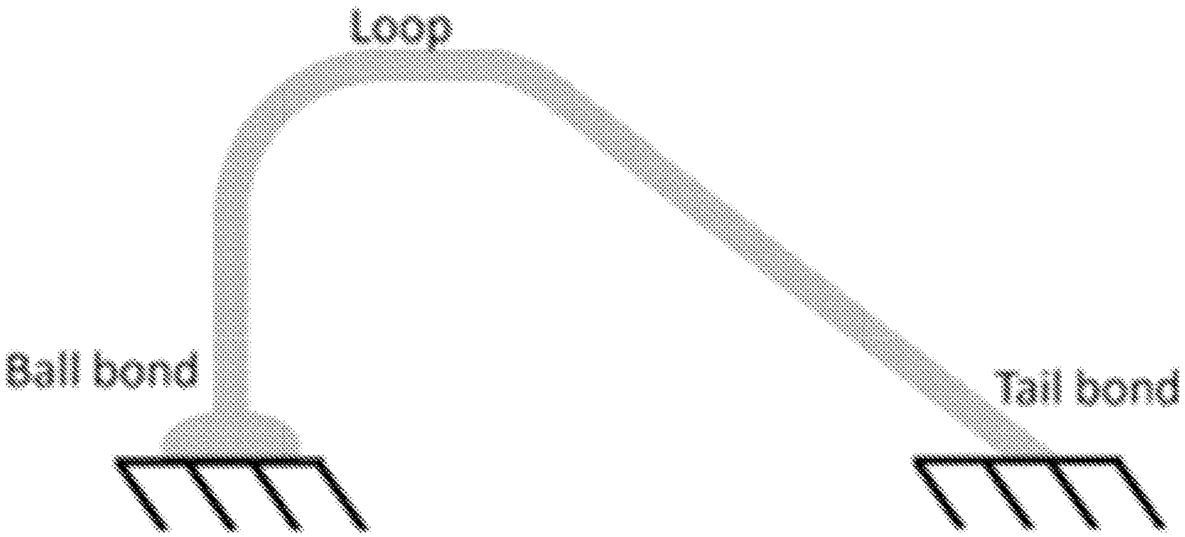
FIG. 7 schematically illustrates an exemplary bonding process, in accordance with some embodiments.

Wire bonding can be used to make the electrical interconnections between active electronics and the electrodes in an array. One example of a wire bond is shown in FIG. 7. A ball bond is simply a wire bond, where the wire has been cut off before making the loop and tail bond. The ball bonding process can use a combination of heat, pressure, and ultrasonic energy to make a connection. Gold is one example of a material that can be used to make a ball bond because is it highly resistant to oxidation.

Figure 8:
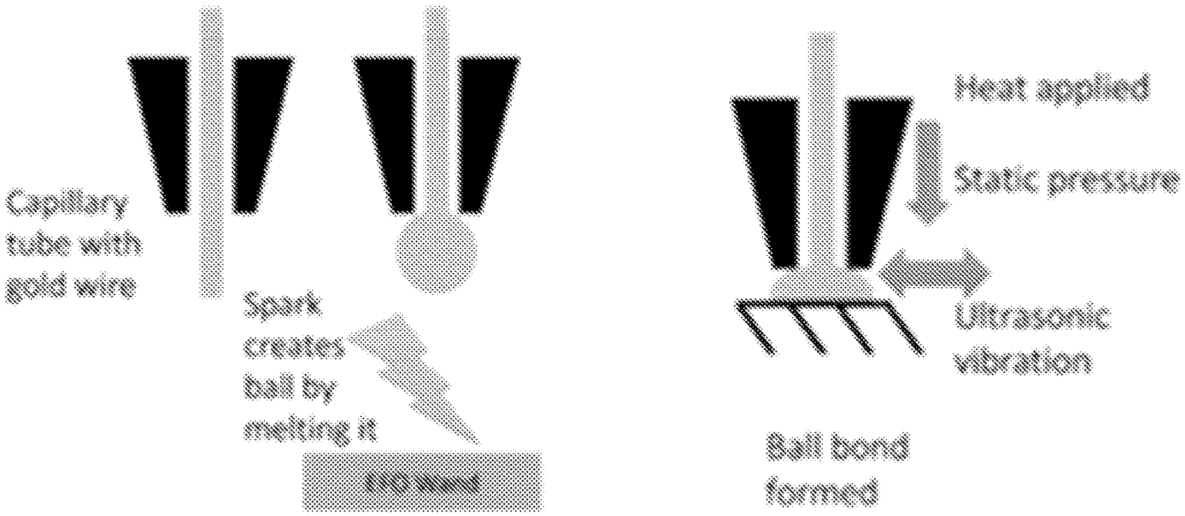
FIG. 8 schematically illustrates an exemplary bonding process, in accordance with some embodiments.
Figure 9:
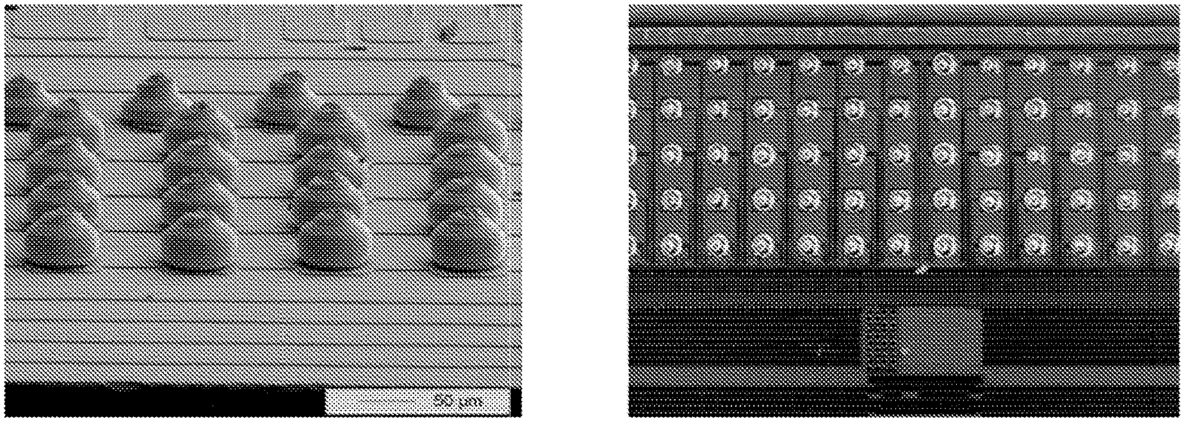
FIG. 9 schematically illustrates an exemplary array of ball bonds, in accordance with some embodiments.

FIG. 8 schematically illustrates the ball bonding process. A high-voltage electric charge can be applied to a gold wire. This can melt the wire at the tip of the capillary tube. The tip of the wire can form into a ball because of the surface tension of the molten metal. The ball quickly solidifies, and the capillary is lowered to the surface of the substrate, which is typically heated to at least 125° C. The machine can then push down on the capillary and apply ultrasonic energy with an transducer. The combined heat, pressure, and ultrasonic energy can create a weld between the ball and the surface of the chip-which is usually coated with a thin film to present the proper material to form the ball bond. In the final step, the machine pays out a small length of wire and tears the wire from the ball using a set of clamps. The cycle then starts again with the high-voltage electric charge being applied to this tail. This process can be repeated automatically using a predefined pattern to create an array of ball bonds as shown in FIG. 9. In some cases, the array of ball bonds can be arranged in a lateral configuration comprising one or more rows or columns. In some cases, the array of ball bonds can be arranged in a pre-determined pattern.

Thin Films

One or more thin films may be deposited on a surface portion of the elongated portions/pillars formed from the source material. The thin films may comprise one or more layers of material deposited on a bulk substrate to impart properties that are not realized by the base material. Thin film deposition can include any action of applying a film of any substance on a surface. Thin films can be stacked on top of each other in unlimited number and configurations to achieve the desired transition of properties from the bulk material to the final surface.

Thin films are generally thin. This can mean anything from a few nanometers (nm) to several microns. Because these films are typically very thin compared to their substrates, graphical representations of thin films that follow are purposefully drawn thicker for clarity. Many thin films can be semitransparent because they are so thin. In some embodiments, the thin films may be semitransparent. In some embodiments, the thin films can be transparent. In some embodiments, the thin films can be opaque.

The thin films can be deposited by many different processes or combinations thereof. This can include but is not limited to physical vapor deposition (PVD), chemical vapor deposition, electroplating, and/or atomic layer deposition.

In some cases, two different thin film stacks can be used when manufacturing electrode arrays. Both films can serve the same purpose but because the starting substrate is a different material, it can take a different thin film stack to accomplish the same goal. The goals of each thin film stack are to transition the substrate surface properties, whatever they may be, to a smooth gold surface which can be used to form a gold-to-gold diffusion bond to another part that has also been treated with a thin film stack that ends with a gold surface.

Thermocompression/Thermosonic Bonding

Thermocompression bonding, also known as diffusion bonding or diffusion welding, can refer to a solid-state welding technique capable of joining similar and dissimilar metals. It operates on the principle of solid-state diffusion, wherein the atoms of two solid, metallic surfaces intersperse themselves over time. This can be accomplished at an elevated temperature, approximately 50-75% of the absolute melting temperature of the materials. Thermocompression bonding can be implemented by applying high pressure, in conjunction with high temperature, to the materials to be welded. Thermosonic bonding can be performed similarly except that some lateral ultrasonic energy can be added to the process. Thermosonic and thermocompression bonds will simply be referred to as bonds for simplicity.

One bond that can be utilized to manufacture the presently disclosed electrodes is a gold-to-gold bond. A gold-to-gold diffusion bond can be highly conductive, biocompatible, biostable, and mechanically robust. Almost any combination of materials can be bonded using a gold-to-gold bond if the appropriate thin film stack is applied to the surfaces that need to be bonded.

Figure 10:
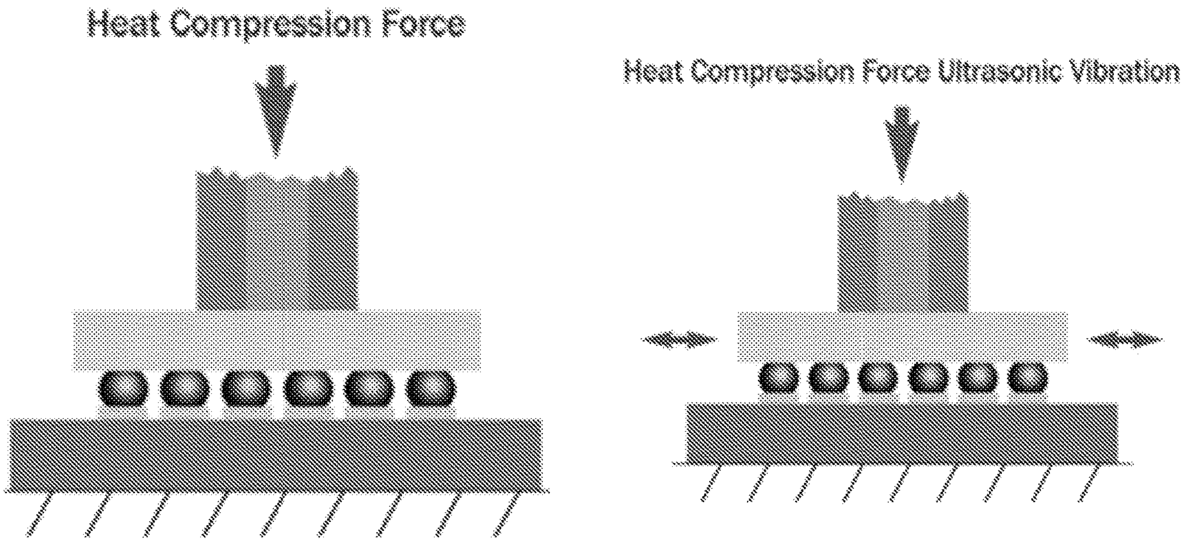
FIG. 10 schematically illustrates bonding of two distinct parts having different functions and/or material properties, in accordance with some embodiments.

When thermocompression bonding is utilized in combination with an array of gold ball bumps and a flip chip bonding machine, two distinct parts having different functions and/or material properties can be bonded and/or electrically coupled as shown in FIG. 10.

Hermetic Feedthroughs

The elongated features may be electrically coupled to one or more hermetic feedthroughs using the methods disclosed herein. A hermetic feedthrough can be a "connector" that establishes a connection between two different environments. Hermetic feedthroughs can be used to protect electronics from the harsh environment of the body. This isolation can be achieved by packaging the electronics in a hermetic package, a package that is perfectly (hermetically) sealed to prevent water, gases, or any other materials from entering the package that could damage the electronics. The hermetic feedthrough can be part of a package, and can allow electrical signals to pass into and out of the package as needed while maintaining a hermetic seal. Many different types of medical hermetic feedthroughs exist and can be purchased as stock components or custom made by many different suppliers.

Figure 11:
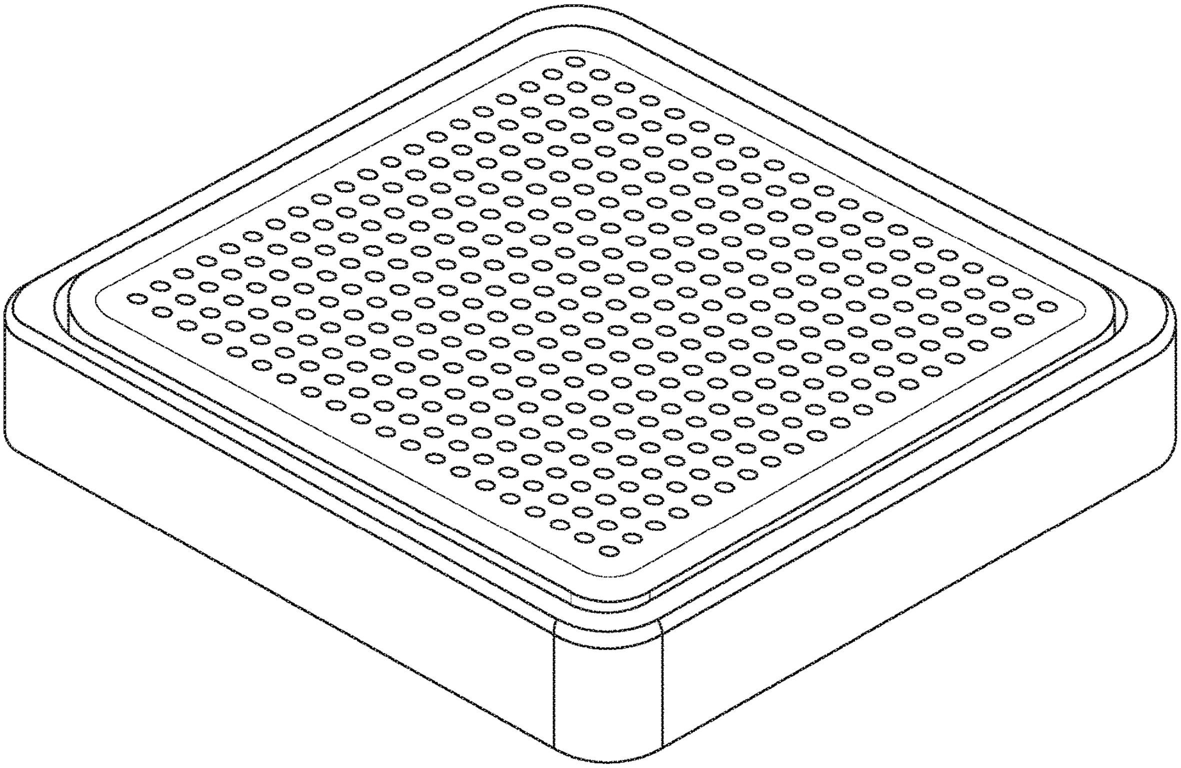
FIG. 11 schematically illustrates an exemplary feedthrough, in accordance with some embodiments.

Several different feedthroughs can be used to achieve a very high/dense channel count. FIG. 11 illustrates an exemplary feedthrough. The center part can comprise an alumina ceramic with a plurality of small holes drilled into it to form a plurality of vias. Each via can be filled with a mixture of platinum and alumina before the center part is fired to its final specifications. This can create a hermetic seal along the inside edges of each via, making the entire alumina piece hermetic.

In some cases, the part can be gold brazed into a titanium flange. The gold braze process can be beneficial because an alumina surface will not usually bond with gold unless it is "metallized". This metallization can be a thin film stack that modifies the surface properties of the alumina so that it will bond to gold. This can provide a hermetic seal between the titanium flange and the alumina.

Figure 12:
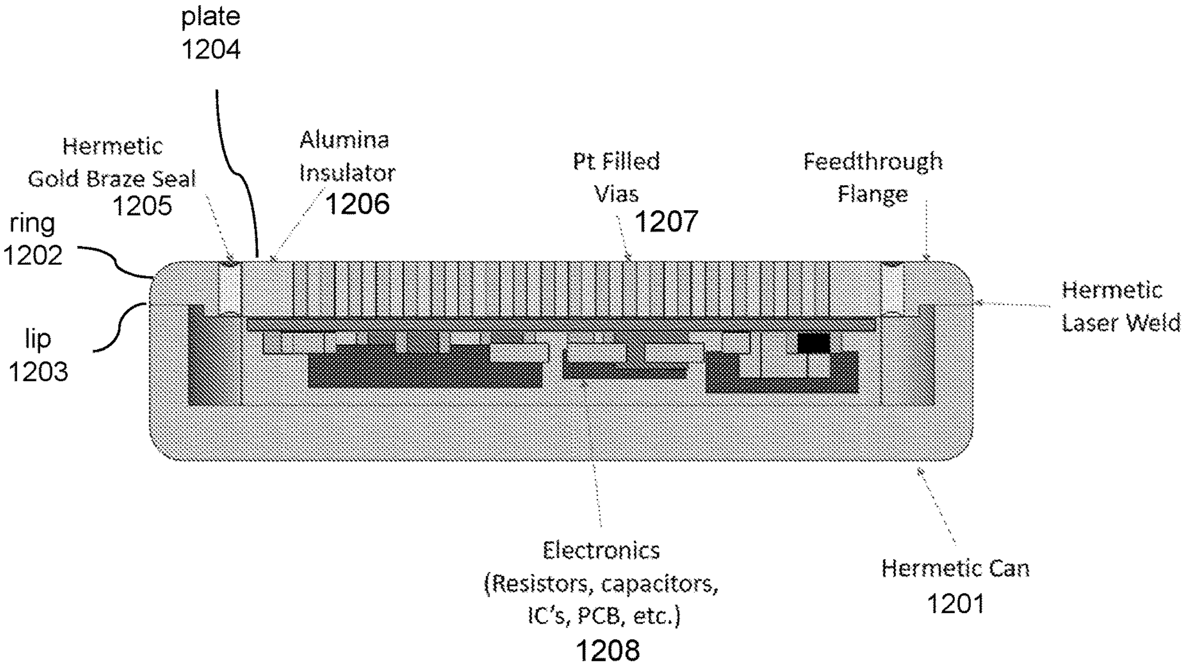
FIG. 12 schematically illustrates an exemplary hermetic packaging comprising active electronic components, in accordance with some embodiments.

In some instances, a second piece (typically called a can), can be laser welded to the feedthrough to create a hermetic package. Active electronics can be placed inside the package, as shown in FIG. 12, where they will be protected from the body while maintaining electrical communications to the outside electrodes.

Laser Machining

Figure 13:
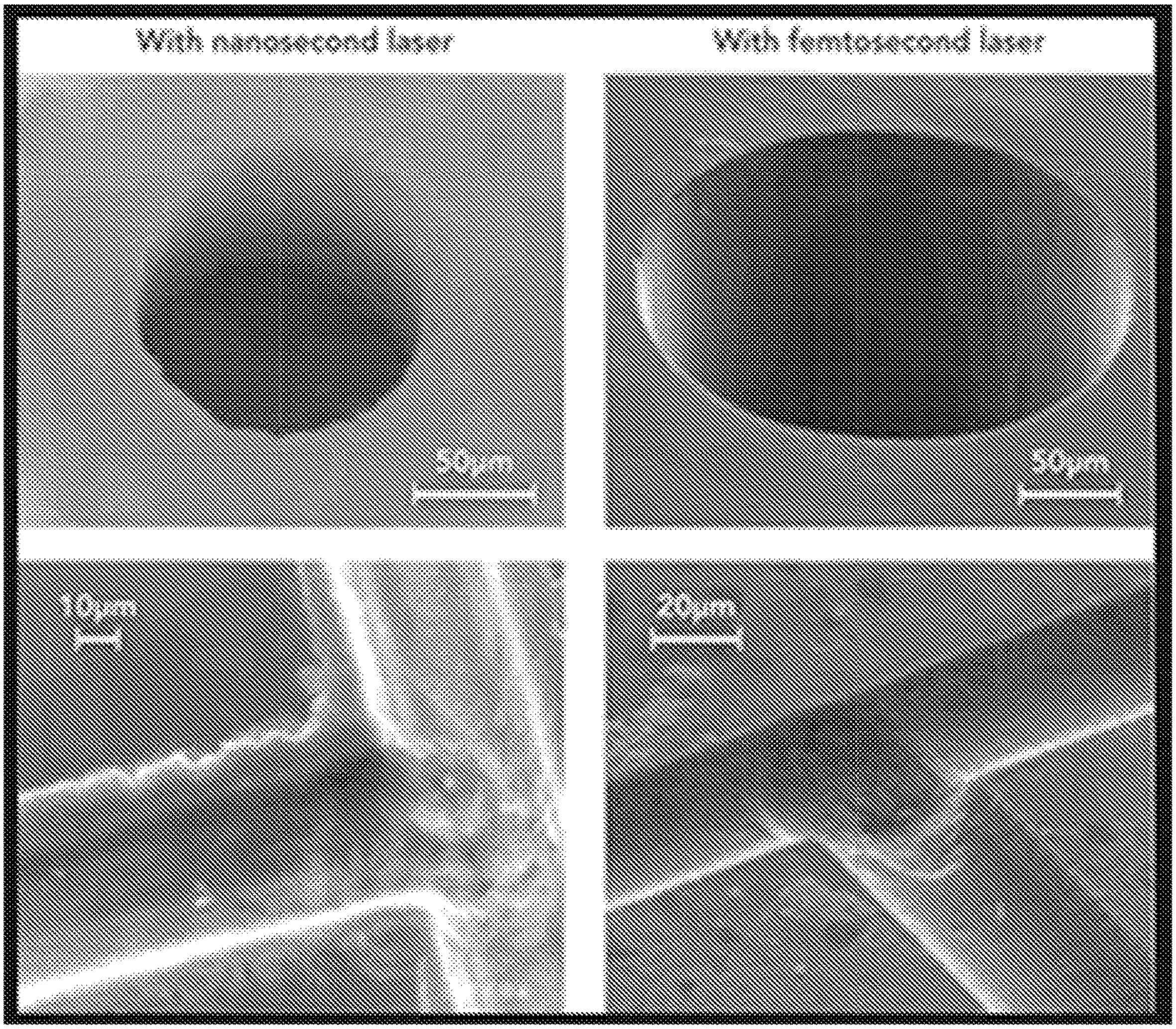
FIG. 13 schematically illustrates an exemplary laser machining process, in accordance with some embodiments.

Lasers can be used to machine parts. This process can be highly accurate and controllable as shown in FIG. 13. The major difference between the left-hand and right-hand images is the pulse width of the laser. Both types could be used for our purposes, but a femtosecond laser is preferred because the heat affected zone is smaller, and there is less recast. Other laser parameters, such as focal length, wavelength, frequency, beam spot size, etc. can be controlled and chosen to optimize the cut based on the substrate material and any thin films that might be applied to achieve the desired material removal.

Figure 14:
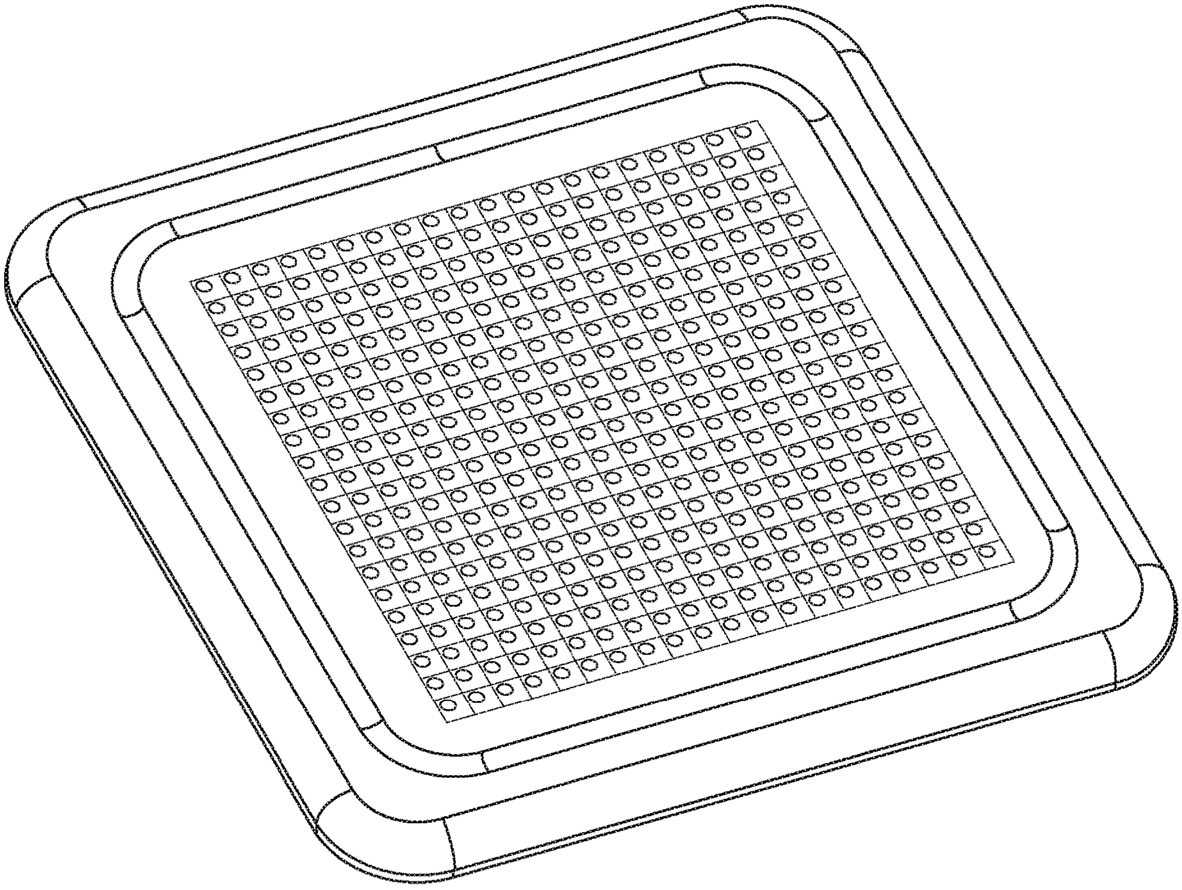
FIG. 14 schematically illustrates an exemplary feedthrough where a transparent gold thin film has been removed from the surface of a ceramic feedthrough with minimal damage to the underlaying ceramic.

If the laser machining equipment is fitted with a scan cube and/or translational stages, it can create 2D patterns of shallow cuts as shown in the bottom right panel of FIG. 13. FIG. 14 shows another exemplary feedthrough where a transparent gold thin film has been removed from the surface of a ceramic feedthrough with minimal damage to the underlaying ceramic. Prior to laser machining, the thin film connects each of the vias electrically, but after the pattern is cut by the laser, each via can be electrically isolated. The exact pattern machined into the part is extremely flexible and scalable.

Methods

Figure 15:
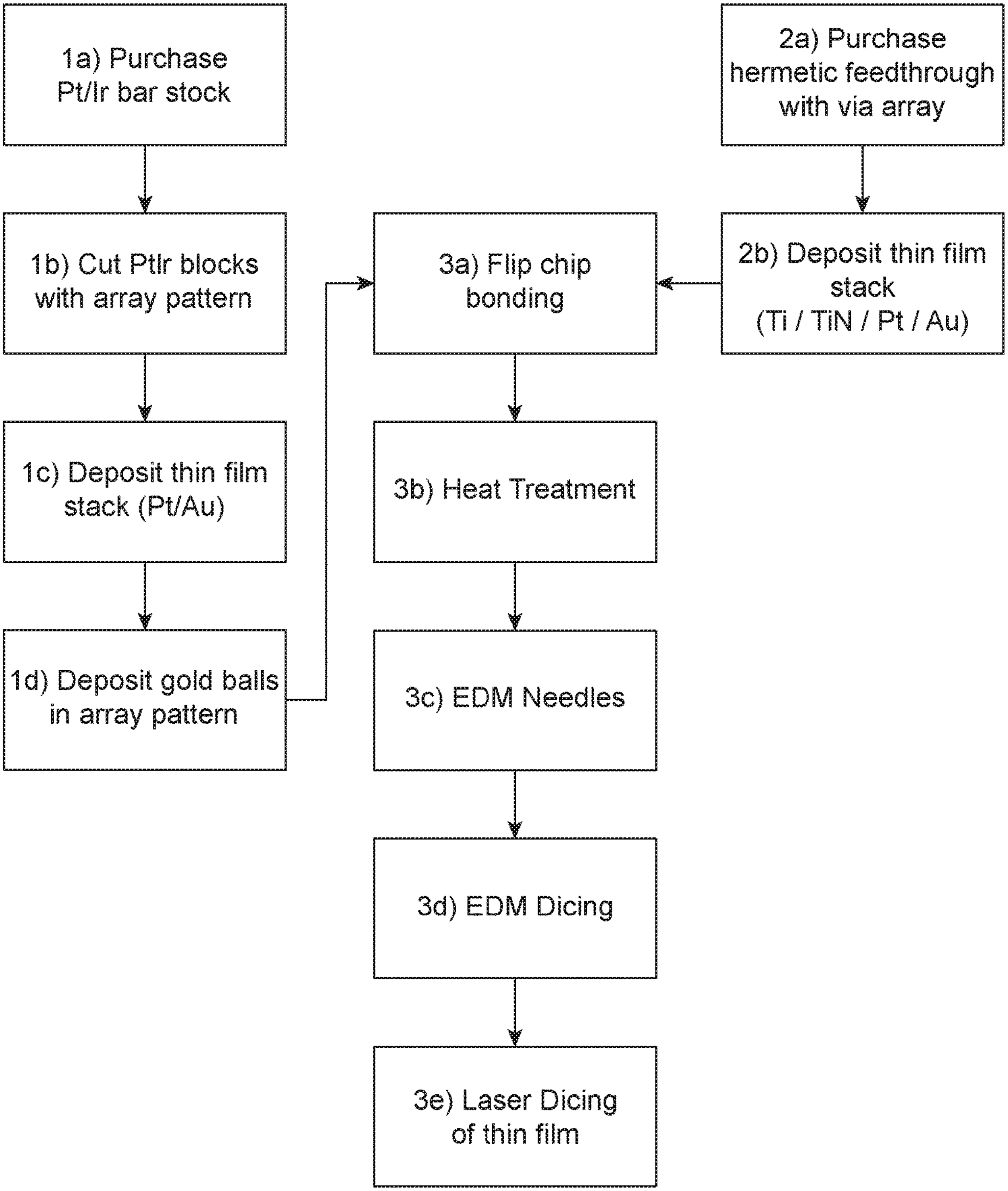
FIG. 15 schematically illustrates a flow chart of an exemplary process for manufacturing an array of electrodes, in accordance with some embodiments.

The techniques and methodologies described above may be utilized in combination with each other to form a high-density array of electrodes bonded to the feedthrough vias of a hermetic feedthrough. Active electronics can then be bonded to the other side of the feedthrough and encased in a hermetic package. FIG. 15 illustrates a flow chart of an exemplary process for manufacturing an array of electrodes.

In some embodiments, a source material (e.g., Pt/Ir) can be acquired. The source material may comprise an alloy comprising 90% Platinum, 10% Iridium, in an annealed state (PtIr). The bar can be about 8 mm×8 mm×200 mm which is sufficient to make roughly 150-200 electrode arrays. This material is biocompatible, biostable, electrically conductive and excellent for use in picking up small electrical spikes or signals created by individual neurons. Other metals and/or alloys could be substituted.

Figure 16:
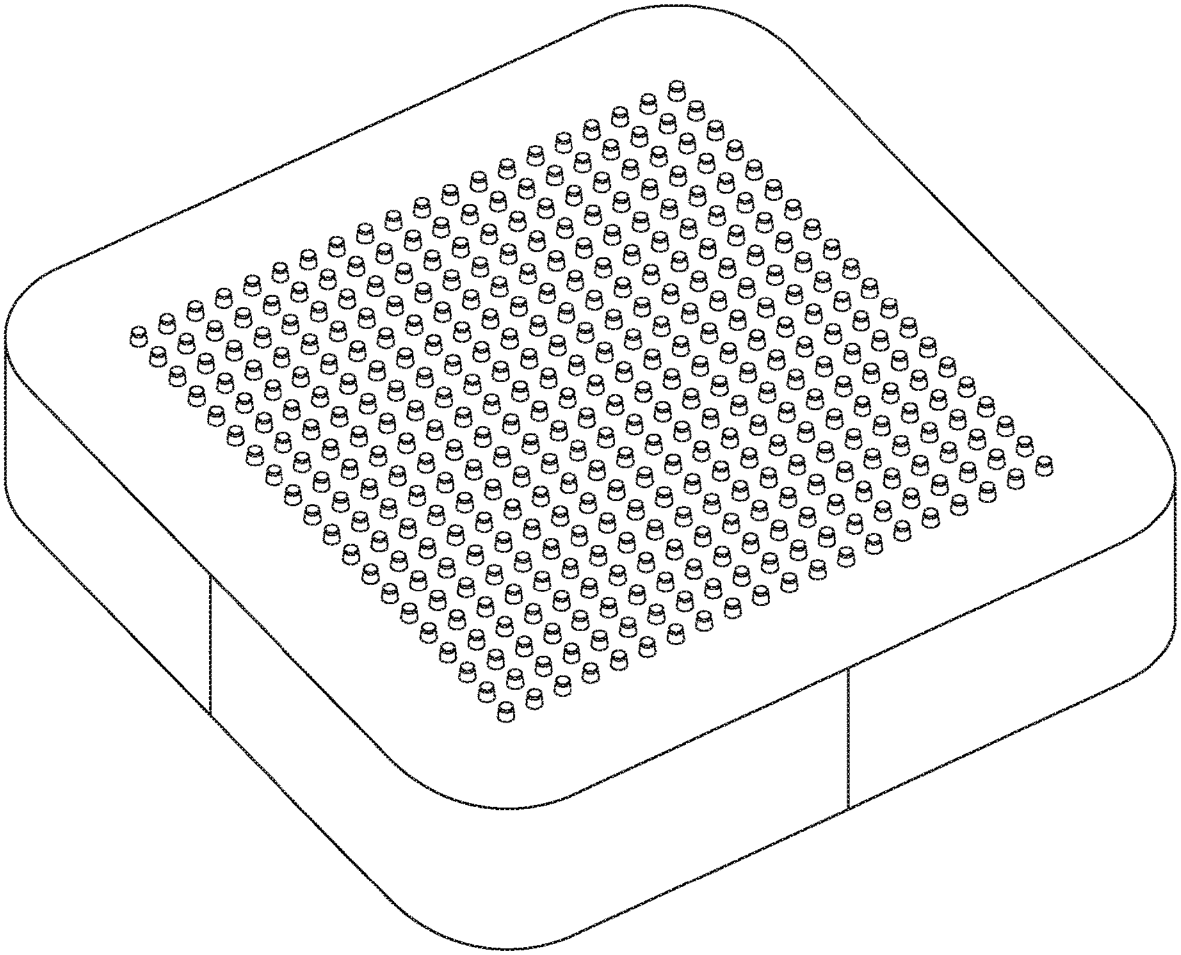
FIG. 16 schematically illustrates an exemplary array of pillars that can be formed from a source material, in accordance with some embodiments.

The PtIr blocks can be cut with an array pattern. The PtIr bar stock can be cut down to about 8 mm×8 mm×2 mm. After cutting to size, a laser machining process can be used to cut one or more elongated features (e.g., "pillars") into one side of the part. Other machining techniques could be substituted. The pillars can be arranged in the same pattern as the final electrode array. In some cases, the pillars can be approximately 3 times the diameter of the EDM wire that will be used. The height of the pillars is important because in a later step, the wire in the EDM machine will need to cut all the way through the PtIr block but it cannot touch the feedthrough. This height can provide enough gap space to allow this to occur reliably. In some cases, the array may comprise 400 pillars, arranged in a 20×20 array where each pillar is approximately 150 μm in diameter and 150 μm tall. A model of this is shown in FIG. 16.

In some cases, one or more thin films (e.g., a Pt/Au thin film stack) can be deposited on the pillars. This part can eventually be bonded to a feedthrough. This bond can comprise a gold-to-gold thermocompression bond. Since the metal block is PtIr, a thin film stack can be deposited using a PVD process to transition the top surface of each PtIr pillar to adhere to gold. During the PVD process, the part can be masked so that only the tops of the pillars are coated but this is not completely necessary and there is no issue simply coating the entire surface shown in FIG. 16. In some cases, the Pt layer is approximately 10 nm thick and its function is to provide a uniform surface for the next layer. A layer of gold, approximately 1200 nm thick can then be applied using a PVD process. Other thin film deposition processes could be used to similar effect. The thin film stack could also be modified (materials, thicknesses) as long as a good adhesion of the gold stack is maintained, and all materials used are both biocompatible and biostable.

In some embodiments, gold balls may be deposited into an array pattern. Using a wire bonding machine with gold wire approximately 50-100 μm in diameter, one gold ball can be deposited on top of each pillar. The ball diameter can be slightly smaller than the diameter of the pillar.

The elongated features/pillars may be electrically coupled to a hermetic feedthrough comprising an array of vias extending through at least a portion of the feedthrough. The feedthrough may comprise a conductive material on the perimeter so that it can be grounded to an EDM machine when clamped to the worktable. In one case, the ceramic can be metallized and then gold brazed into a titanium flange that can be conductive. If this were a 100% ceramic part, the edges may need to be metallized with a thin film. Any other method used to clamp the part to the EDM worktable and ground the part would be acceptable.

In some cases, one or more thin films may be deposited on the outside surface of the feedthrough. The outside surface of the feedthrough can be modified to a gold layer via a thin film stack. This stack can be different from the stack used to transition the PtIr block to gold because the base material can comprise alumina, and in some cases, not comprise PtIr. Transitioning from a non-conductive ceramic to gold can be more difficult so a more complex thin film stack can be used. One example of a material stack used to transition from a silicon wafer to gold is a 4-layer stack comprising 100 nm titanium, 25 nm titanium nitride, 200 nm of platinum, and 600-1500 nm of gold. This stack can work well with an alumina feedthrough. The reason for the first additional layer (Ti) is to form a good bond with the alumina. Titanium oxidizes readily and there is plenty of oxygen present on the surface of the alumina ($Al_2O_3$). A second additional layer is needed because titanium diffuses quickly into the grain boundaries of platinum and into gold. If this diffusion were to occur, titanium dioxide would form on the surface of the gold and make any gold-to-gold bonds unstable.

It is possible that the thin film stack applied is identical to the thin film stack used to metallize the aluminum for the gold brazing process. However, any thin film stack could be used on the alumina surface at both locations if the stack provides a compatible surface for bonding to gold, has good adhesion between layers, is biocompatible, is biostable, and does not suffer from detrimental effects of diffusion processes across layers.

Figure 17:
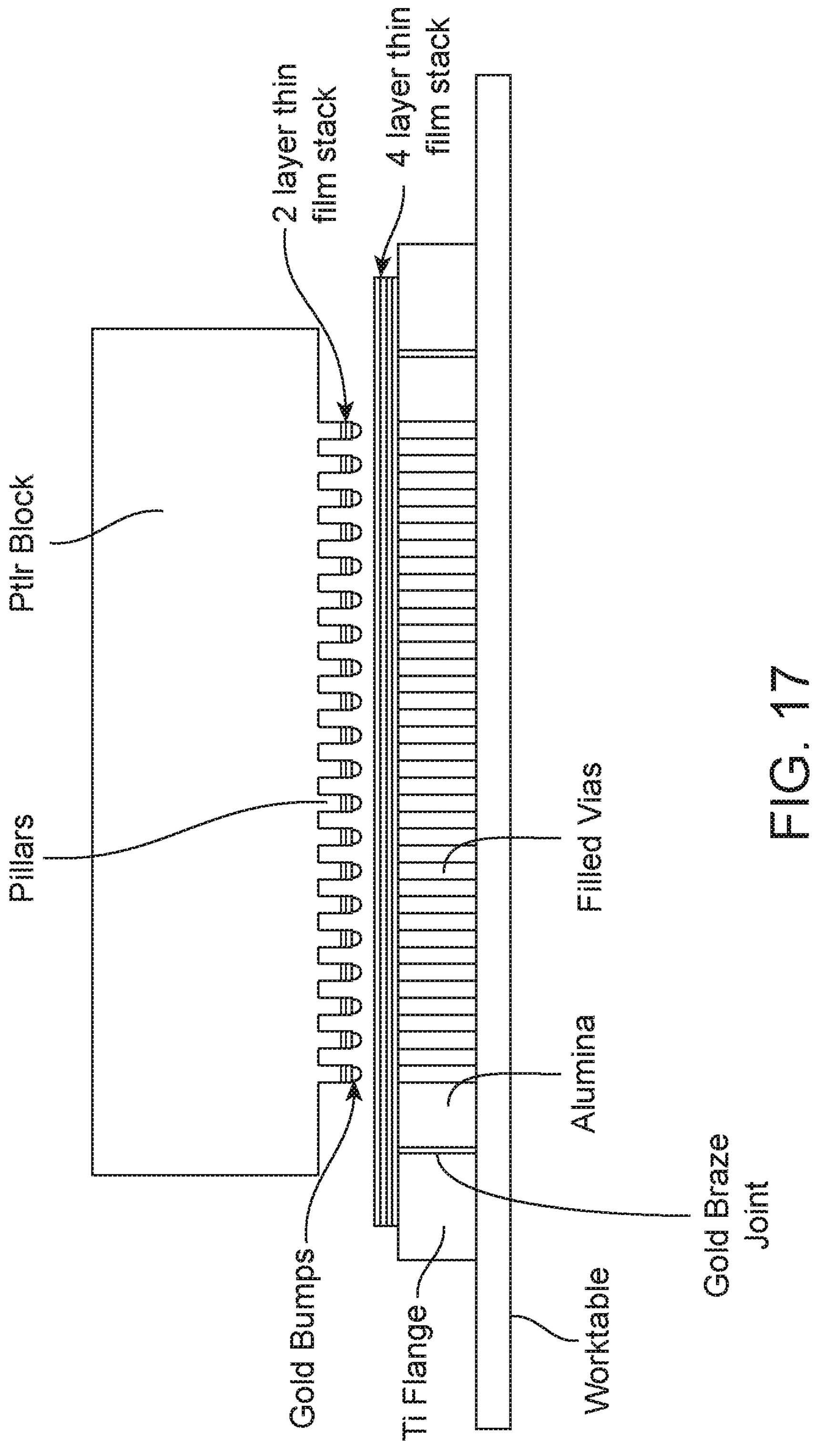
FIG. 17 schematically illustrates a cross section of the two parts before and after thermocompression bonding.
Figure 18:
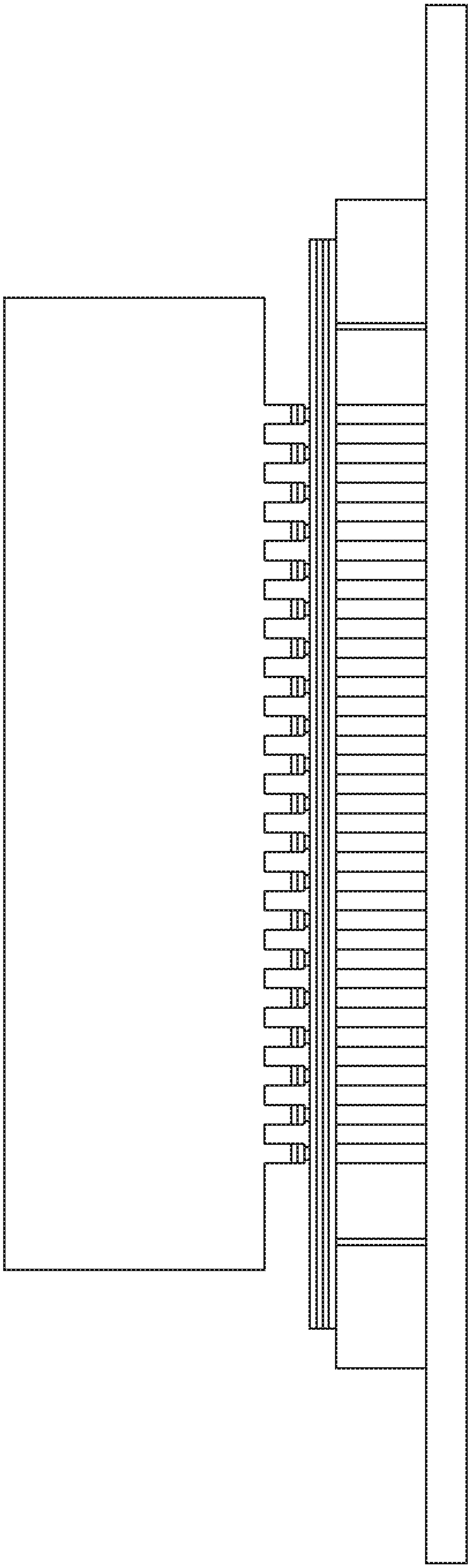
FIG. 18 schematically illustrates a part that can be formed by flip chip bonding, in accordance with some embodiments.

In some embodiments, flip chip bonding can be used to bond the feedthrough to the PtIr block. With the feedthrough and PtIr block properly prepared, both parts can be placed into a flip chip bonding machine and the vias on the feedthrough and the gold bumps on the PtIr block can be aligned using split beam optics. Since this is an optical process, it is important that the vias on the feedthrough are visible through the applied thin films. A cross section of the two parts before and after thermocompression bonding is shown in FIG. 17. Some details of actual parts have been eliminated for clarity. Additionally, the thin film thickness is approximately 50× the actual thicknesses. FIG. 18 shows the same setup after the flip chip bonding. One change is that the parts are now bonded together and the gap between parts can be slightly less due to compression of the gold ball bumps.

In some cases, the parts may undergo a heat treatment. This step is not required but may improve the strength of the gold-to-gold bonds. The part can be placed in a furnace at elevated temperatures for a period to improve diffusion across the bond and relieve any residual stresses. Alternatively, the parts can be placed in a heated press. One difference can be the addition of some compressive forces to improve the diffusion bond.

Figure 19:
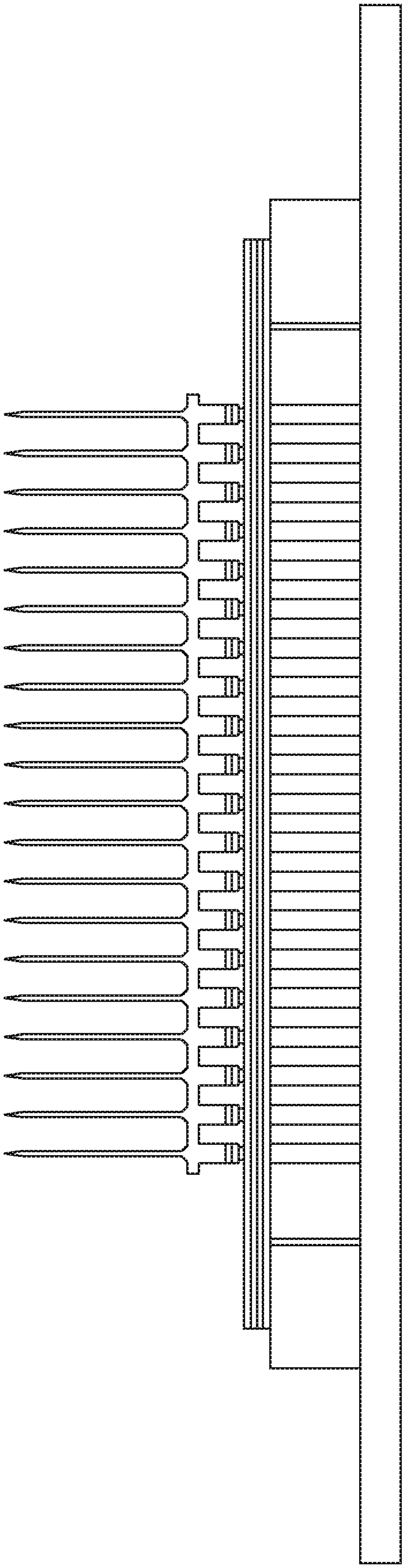
FIG. 19 schematically illustrates an array of needles that can be cut to form a desired tip style, in accordance with some embodiments.

The needles may now be machined from the elongated features/pillars (e.g., using EDM). One or more cuts can be made using WEDM to form needles/electrodes having a desired tip style. The part can be placed into a WEDM machine and secured to the worktable with a clamp. This clamp must be electrically conductive and will ground the assembly to the EDM machine. Cutting paths can be programmed into the EDM machine, and the programs can be run. The result is shown in FIG. 19. If these cuts are made in two dimensions, then the part would look like the needle array shown in FIG. 1 except it is now bonded to a feedthrough via a series of gold bumps and two thin film stacks.

Figure 20:
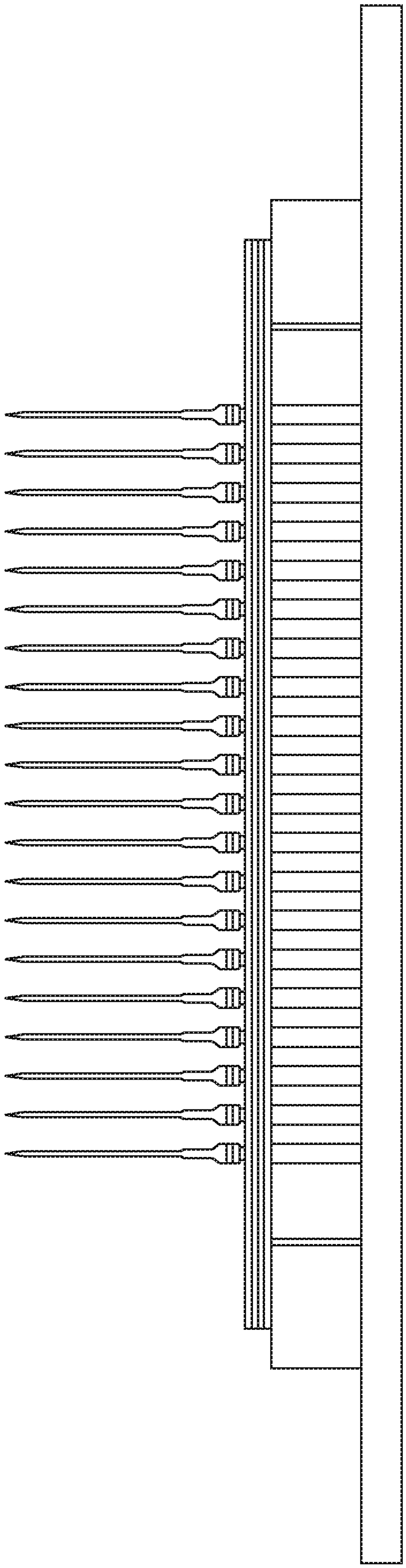
FIG. 20 schematically illustrates a dicing operation that can be performed to produce an array of electrodes.

The part may thereafter undergo WEDM dicing to form an array comprising discrete electrodes. A second set of WEDM cuts can dice the needle array. Dicing is a term used in the semiconductor industry when a large wafer is "diced" into a multitude of single chips. In this case, the needle array can be "diced" into separate needles, each bonded to the metallization layer of the insulator. The result of the second cut is shown in FIG. 20.

In some cases, the dicing step could be accomplished by other means. Some example processes include laser cutting, electrochemical machining, and mechanical dicing with a dicing saw. After this cut, all electrodes are still grounded to the worktable and each other through the gold bumps and the metallization layer. This series of cuts is only possible because of the existence of the thin film stack on top of the feedthrough.

Figure 21:
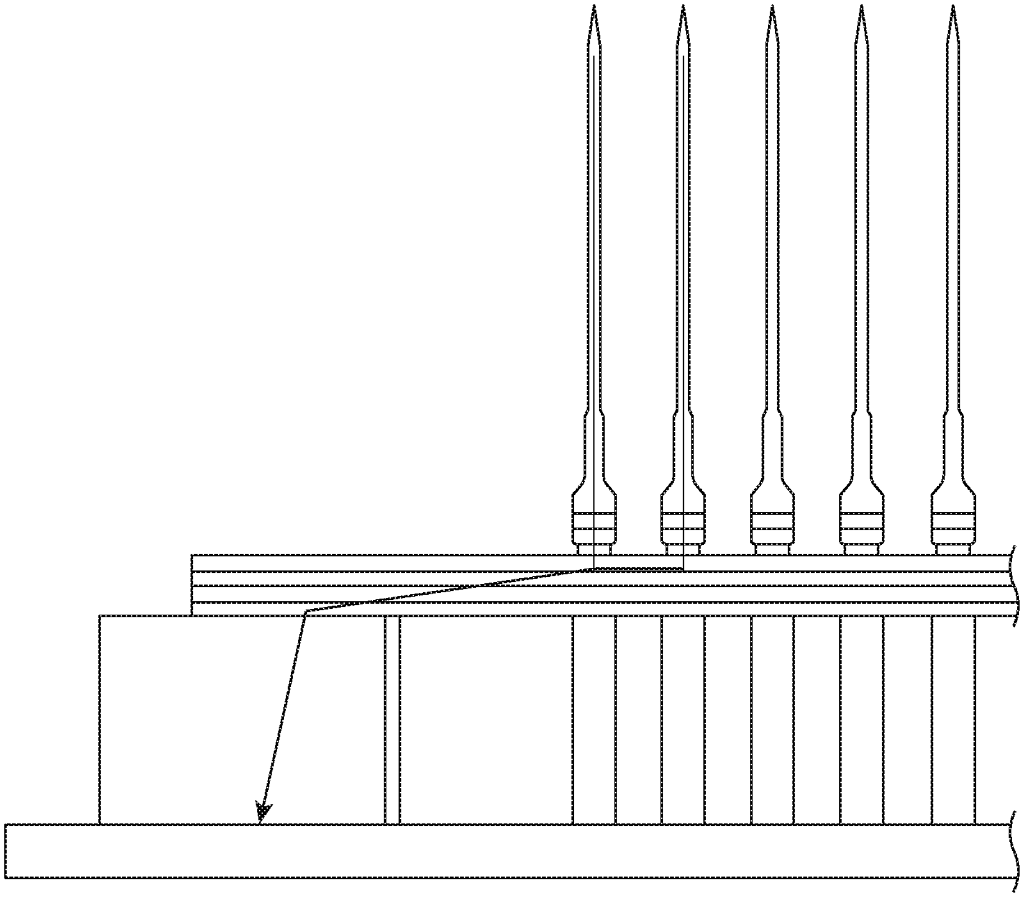
FIG. 21 schematically illustrates the path of electricity from needles to the worktable during EDM, in accordance with some embodiments.

In FIG. 21, the path of electricity from the needles to the worktable is shown by the trajectory of the arrow. The needles can now be physically separated but each can still be electrically connected to the worktable and the other needles of the array through the thin film on the feedthrough and gold bumps. Without the thin film and gold bumps, this final WEDM cut could be very difficult to make. In some cases, a front-side sacrificial layer can be used to shunt away current during EDM milling. In some cases, this can prevent corrosion of other layers during milling and avoid putting current through the vias.

Figure 22:
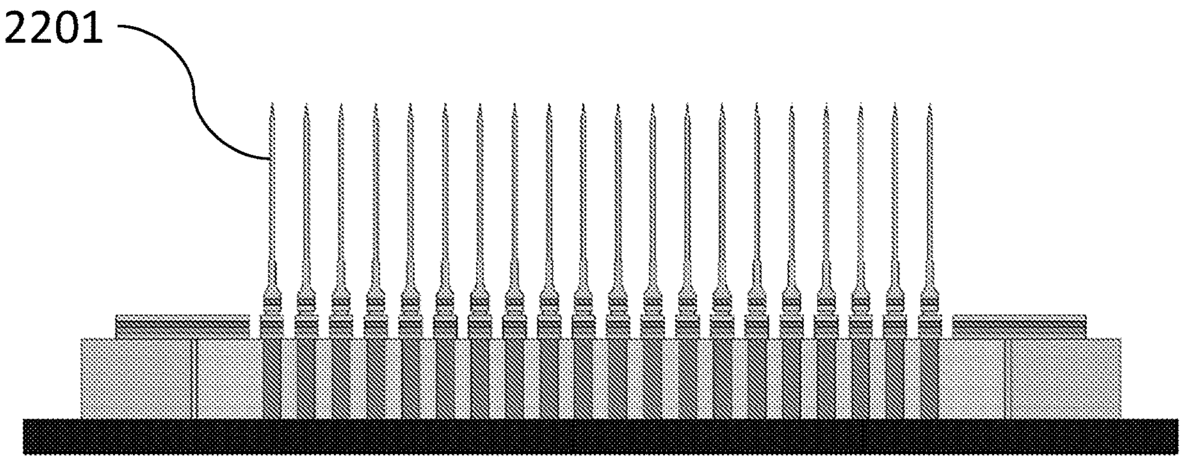
FIG. 22 schematically illustrates an exemplary process of laser machining to dice a thin film layer in a regular pattern around each of the electrodes in an array, in accordance with some embodiments.
Figure 23:
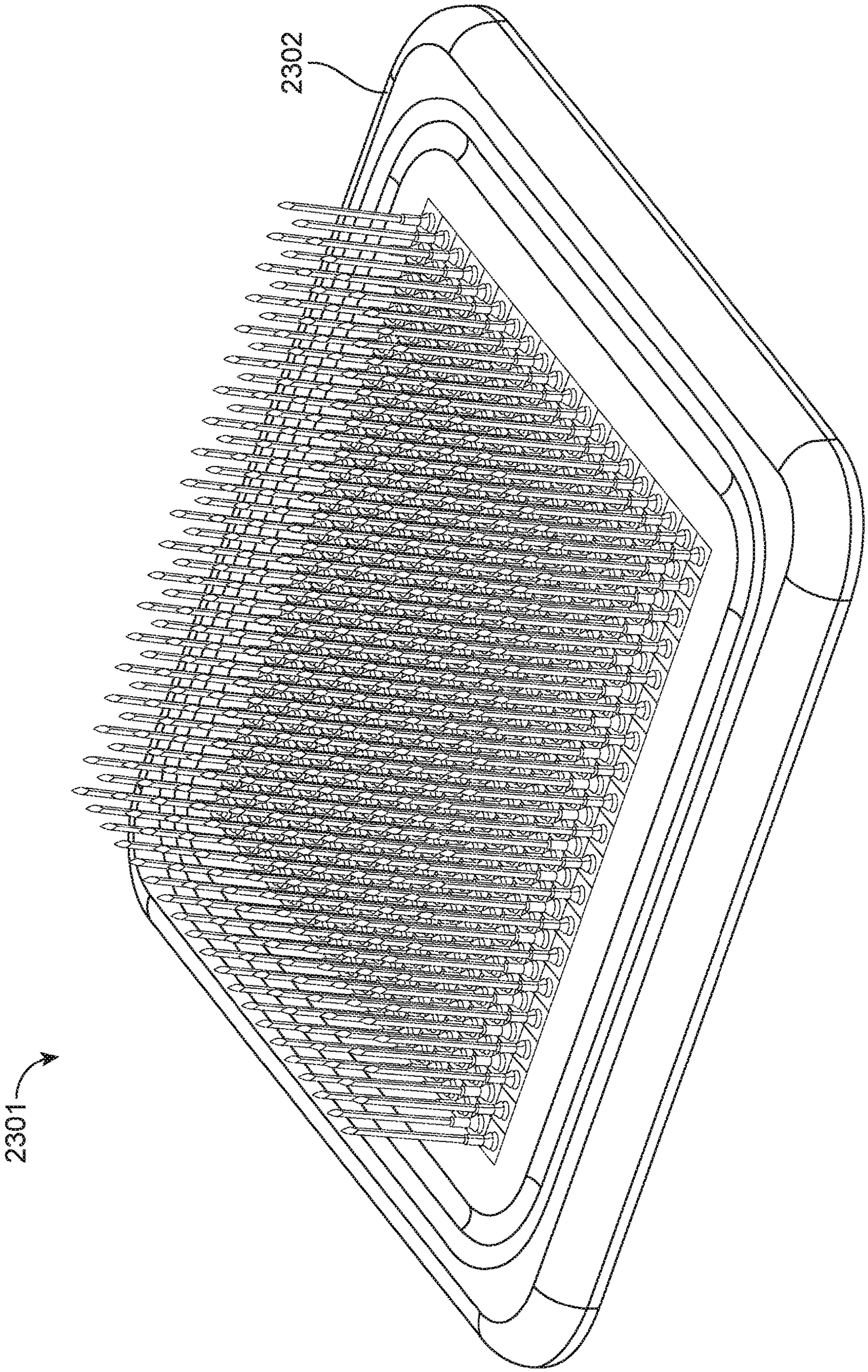
FIG. 23 schematically illustrates an exemplary process of laser machining to dice a thin film layer in a regular pattern around each of the electrodes in an array, in accordance with some embodiments.
Figure 24:
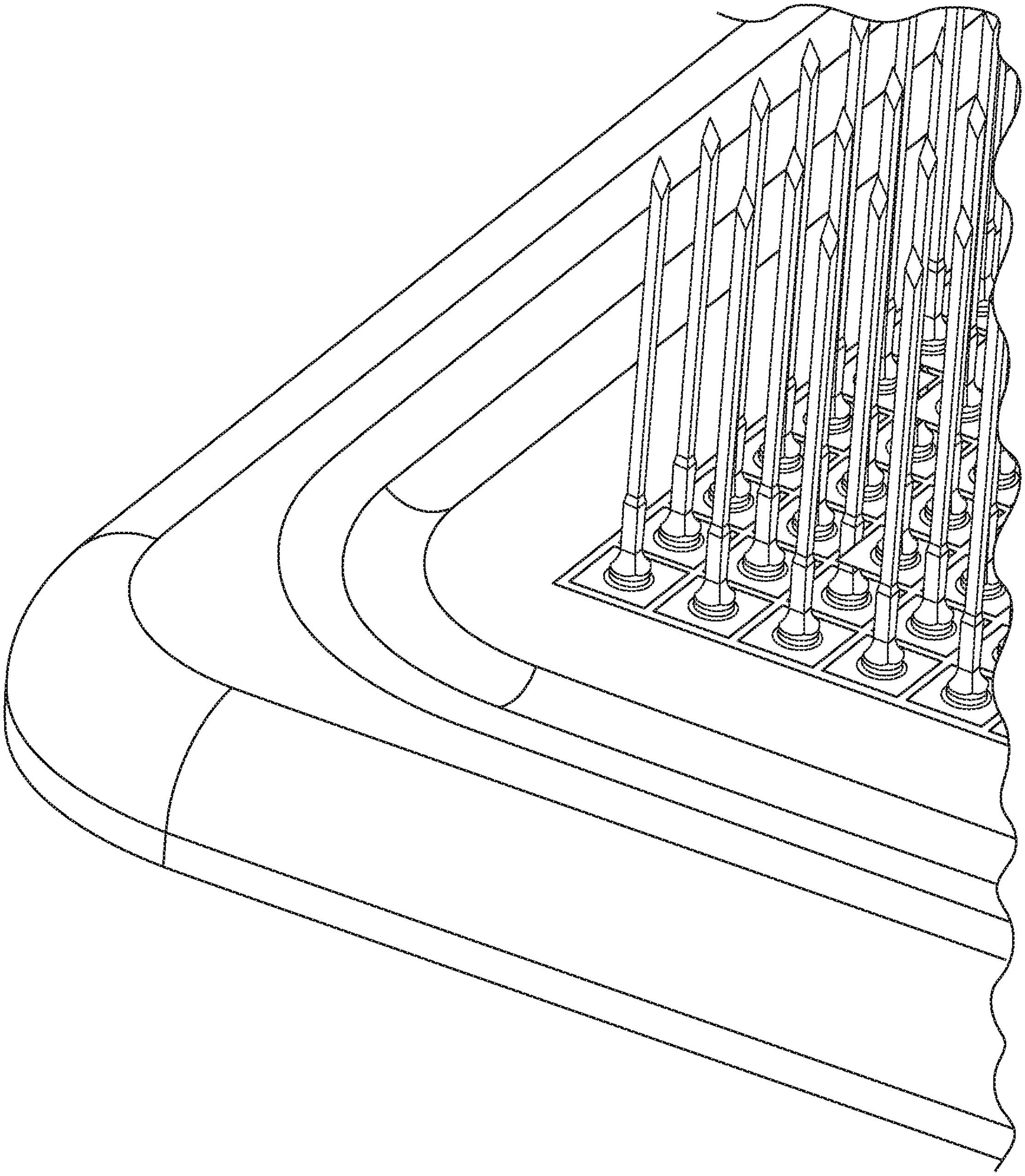
FIG. 24 schematically illustrates an exemplary process of laser machining to dice a thin film layer in a regular pattern around each of the electrodes in an array, in accordance with some embodiments.

In some cases, the method may comprise a step of laser dicing the feedthrough thin film. The final step in the process can be to electrically isolate the needles from each other, transforming them into electrodes. In some cases, this cannot be done with WEDM because the wire would meet the alumina and likely break. Instead, laser machining can be used to dice the thin film layer in a regular pattern around each of the electrodes. This step is shown in FIG. 22, FIG. 23, and FIG. 24, in accordance with some embodiments. In some cases, electrochemical machining (ECM) can be used instead of laser dicing. In any case, the thin films deposited on the feedthrough can be thinned or ablated as needed to isolate the needles and form discrete electrodes.

Implantable Brain-Computer Interface

In some aspects, the present disclosure provides an implantable brain-computer interface (2301). In some cases, the implantable brain-computer interface comprises a hermetically sealed packaging (2302). In some cases, the hermetically sealed packaging comprises a can (1201). In some cases, the hermetically sealed packaging comprises a ring (1202). In some cases, the ring is welded to the lip (1203) of the can. In some cases, the ring is laser-welded to the lip of the can. In some cases, the hermetically sealed packaging comprises a plate (1204). In some cases, the plate is sealed to the ring. In some cases, the plate is sealed to the ring by a gold-braze (1205).

In some cases, the plate comprises an insulating substrate (1206) with an array of holes. In some cases, the insulating substate comprises alumina. In some cases, the plate comprises an array of conductive vias (1207) filling the array of holes. In some cases, the array of conductive vias comprises platinum.

In some cases, the hermetically sealed packaging comprises an active electronic circuit (1208) disposed between the can and the plate, such that the active electronic circuit is hermetically sealed in the packaging. In some cases, the hermetically sealed packaging comprises a wirelessly secondary battery for powering the active electronic circuit;

In some cases, the implantable brain-computer interface comprises an array of needle electrodes (2201). In some cases, the array of needle electrodes are electropolished. In some cases, the array of needle electrodes comprise PtIr. In some cases, the array of needle electrodes are in electromagnetic communication with the array of conductive vias. In some cases, the array of needle electrodes and the array of conductive vias are interposed by one or more layers.

Figure 28:
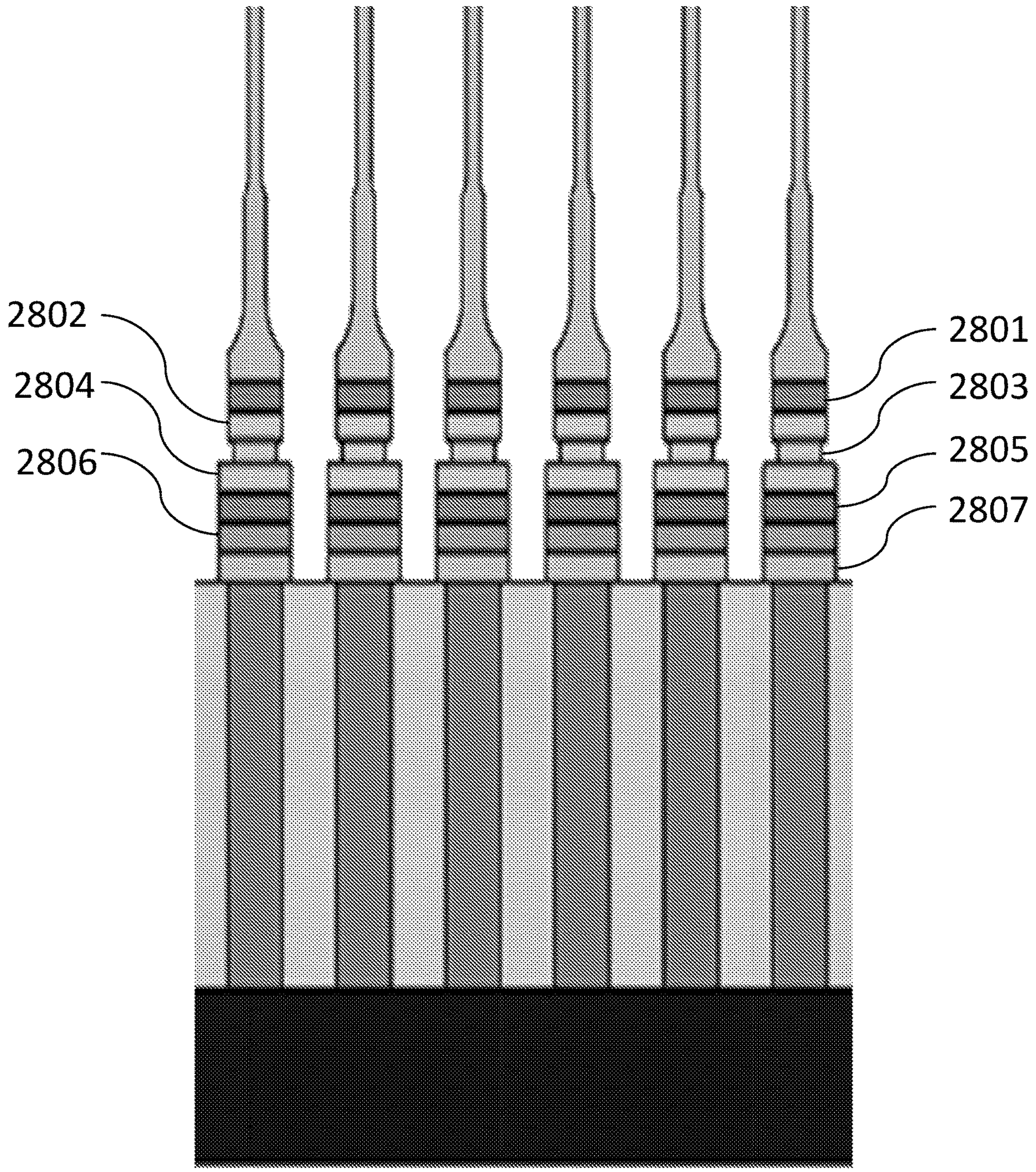
FIG. 28 schematically illustrates an implantable brain-computer interface, in accordance with some embodiments.

FIG. 28 schematically illustrates an implantable brain-computer interface. In some cases, the one or more layers comprise a titanium layer (2807). In some cases, the titanium layer is adjacent to the array of conductive platinum vias. In some cases, the titanium layer is at least 10, 20, 30, 40, 50, 60, 70, 80, 90, 100, 200, 300, 400, or 500 nm thick. In some cases, the titanium layer is at most 10, 20, 30, 40, 50, 60, 70, 80, 90, 100, 200, 300, 400, or 500 nm thick.

In some cases, the one or more layers comprise a titanium nitride layer (2806). In some cases, titanium nitride layer is at least 5, 10, 15, 20, 25, 30, 35, 40, 45, 50, 100, or 200 nm thick. In some cases, titanium nitride layer is at most 5, 10, 15, 20, 25, 30, 35, 40, 45, 50, 100, or 200 nm thick. In some cases, the titanium nitride layer adjacent to the titanium layer. In some cases, the titanium nitride layer adjacent to a platinum layer.

In some cases, the one or more layers comprise a platinum layer (2805). In some cases, the platinum layer is at least 50, 100, 150, 200, 300, 400, or 500 nm thick. In some cases, the platinum layer is at most 50, 100, 150, 200, 300, 400, or 500 nm thick. In some cases, the platinum layer is adjacent to the titanium nitride layer. In some cases, the platinum layer is adjacent to a gold layer.

In some cases, the one or more layers comprise a gold layer (2804). In some cases, the gold layer is at least 600, 700, 800, 900, 1000, 1100, 1200, 1300, 1400, or 1500 nm thick. In some cases, the gold layer is at most 600, 700, 800, 900, 1000, 1100, 1200, 1300, 1400, or 1500 nm thick. In some cases, the gold layer is adjacent to the platinum layer. In some cases, the gold layer is adjacent to a gold bump.

In some cases, the one or more layers comprises a gold bump (2805). In some cases, the gold bump is at least 10, 20, 30, 40, 50, 60, 70, 80, 90, or 100 μm thick. In some cases, the gold bump is at most 10, 20, 30, 40, 50, 60, 70, 80, 90, or 100 μm thick. In some cases, the gold bump is adjacent to a second gold layer.

In some cases, the one or more layers comprises a second gold layer (2802). In some cases, the thickness of the second gold layer is about 300 nm to about 1,500 nm. In some cases, the thickness of the second gold layer is about 300 nm to about 500 nm, about 300 nm to about 1,000 nm, about 300 nm to about 1,200 nm, about 300 nm to about 1,500 nm, about 500 nm to about 1,000 nm, about 500 nm to about 1,200 nm, about 500 nm to about 1,500 nm, about 1,000 nm to about 1,200 nm, about 1,000 nm to about 1,500 nm, or about 1,200 nm to about 1,500 nm. In some cases, the thickness of the second gold layer is about 300 nm, about 500 nm, about 1,000 nm, about 1,200 nm, or about 1,500 nm. In some cases, the thickness of the second gold layer is at least about 300 nm, about 500 nm, about 1,000 nm, or about 1,200 nm. In some cases, the thickness of the second gold layer is at most about 500 nm, about 1,000 nm, about 1,200 nm, or about 1,500 nm. In some cases, the second gold layer is adjacent to a platinum layer.

In some cases, the one or more layers comprise a platinum layer (2801). In some cases, the thickness of the platinum layer is about 25 nm to about 250 nm. In some cases, the thickness of the platinum layer is about 25 nm to about 50 nm, about 25 nm to about 75 nm, about 25 nm to about 100 nm, about 25 nm to about 150 nm, about 25 nm to about 200 nm, about 25 nm to about 250 nm, about 50 nm to about 75 nm, about 50 nm to about 100 nm, about 50 nm to about 150 nm, about 50 nm to about 200 nm, about 50 nm to about 250 nm, about 75 nm to about 100 nm, about 75 nm to about 150 nm, about 75 nm to about 200 nm, about 75 nm to about 250 nm, about 100 nm to about 150 nm, about 100 nm to about 200 nm, about 100 nm to about 250 nm, about 150 nm to about 200 nm, about 150 nm to about 250 nm, or about 200 nm to about 250 nm. In some cases, the thickness of the platinum layer is about 25 nm, about 50 nm, about 75 nm, about 100 nm, about 150 nm, about 200 nm, or about 250 nm. In some cases, the thickness of the platinum layer is at least about 25 nm, about 50 nm, about 75 nm, about 100 nm, about 150 nm, or about 200 nm. In some cases, the thickness of the platinum layer is at most about 50 nm, about 75 nm, about 100 nm, about 150 nm, about 200 nm, or about 250 nm. In some cases, the platinum layer is adjacent to the array of needle electrodes.

In some cases, the one or more layers are annealed. In some cases, the one or more layers are thermally annealed. Annealing can increase adhesion between the one or more layers, the array of needle electrodes, and/or the array of conductive vias.

In some cases, the array of needle electrodes comprise a density of at least 1, 2, 3, 4, 5, 6, 7, 8, 9, 10, 20, 30, 40, 50, 60, 70, 80, 90, or 100 needle electrodes per $mm^2$. In some cases, the array of needle electrodes comprise a density of at most 1, 2, 3, 4, 5, 6, 7, 8, 9, 10, 20, 30, 40, 50, 60, 70, 80, 90, or 100 needle electrodes per $mm^2$.

In some cases, the array of needle electrodes comprise at least 10, 20, 30, 40, 50, 60, 70, 80, 90, 100, 200, 300, 400, 500, 600, 700, 800, 900, or 1000 needle electrodes. In some cases, the array of needle electrodes comprise at most 10, 20, 30, 40, 50, 60, 70, 80, 90, 100, 200, 300, 400, 500, 600, 700, 800, 900, or 1000 needle electrodes.

In some cases, the tips of the array of electropolished PtIr needle electrodes comprise a maximum curvature of κ, where κ=1/R, where R is the radius of the osculating circle of the tips. In some cases, κ is at least 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, or $mm^{-1}$. In some cases, κ is at most 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, or $mm^{-1}$. In some cases, the array of needle electrodes comprise a mechanical integrity sufficient to penetrate brain tissue without substantial permanent deformation.

Cleaning

At each step of the process, considerable effort can be spent cleaning the devices before a process is conducted, especially the deposition of the thin films and the bonding steps. At these steps, small levels of impurities, contaminants, water, oxides, etc. can lead to immediate and/or long-term failures of the bonds. Accordingly, each step in the process can utilize specific cleaning steps that can ensure a good process. Examples of cleaning steps that can be used in various orders and combinations include, for example:

- Soak/Rinse in deionized (DI) water
- Soak/Rinse in isopropyl alcohol (IPA)
- Soak in an acid
- Soak in a base
- Soak in an enzymatic solution
- Sonication while soaking
- Drying with an inert gas
- Isolating a process in an inert gas to limit exposure to oxygen and/or water
- Baking at high temperature
- Baking at high temperature in a vacuum and/or under an inert gas
- Exposure to oxygen plasma or argon plasma
- Processes conducted in a clean room environment
- Chemical Etchants
- Ozone exposure These cleaning processes are not assumed to be exhaustive, and other cleaning procedures can be used to achieve the desired results.

Protecting the Device from EDM and/or Laser Machining Recast Material

The WEDM process and/or the laser machining process can cause material to be ablated from the surface. The ablated material can be carried away by process fluids or gases. However, some material can redeposit on the surface of the device as it is processed. The redeposition can be problematic. To counter potential redeposition problems, the process can be sandwiched between a coating step and an etching step. One example of this would be to protect the device before laser dicing by applying a Parylene™ coating to the surface before laser dicing. Any recast material from the process can redeposit onto the Parylene™ coating. After the laser dicing, the Parylene™ coating and any recast material can be removed by an oxygen plasma etch, an argon plasma etch, and/or a wash in DI and/or IPA with sonication. The material used to protect the device is not limited to Parylene™, and may extend to other polymers (e.g. polyimides or waxes), metals (e.g. titanium), or other inorganic or ceramic materials (e.g. silicon dioxide) that can provide the desired removal selectivity and protection for the underlying material.

Offset Bonding

Figure 25:
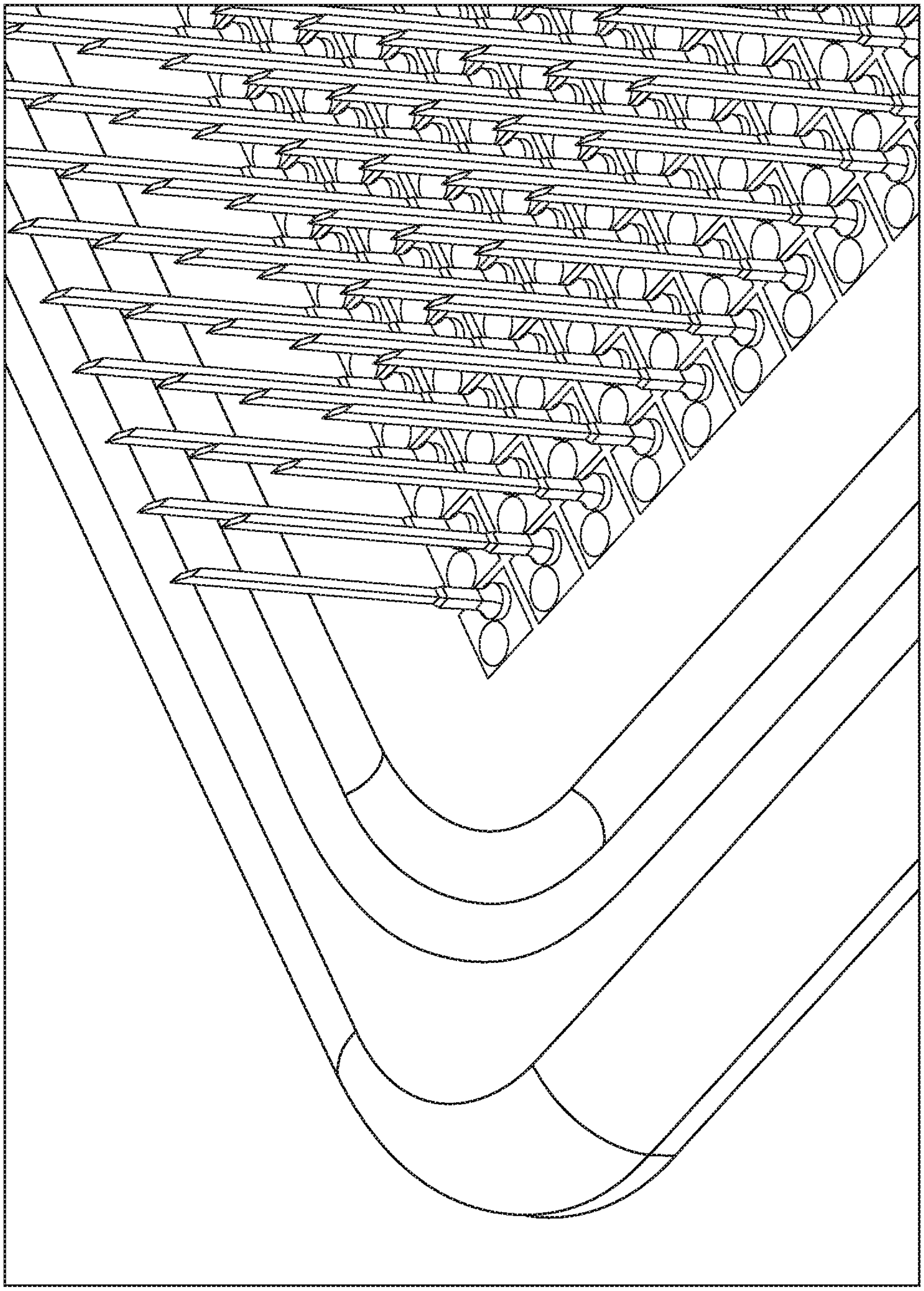
FIG. 25 schematically illustrates an offset between the vias of a feedthrough and the gold balls used to form a gold-to-gold diffusion bind, in accordance with some embodiments.

In some of the embodiments and examples described herein, one or more gold-gold bonds can be created. These bonds can occur directly above the vias in the feedthrough. Each of the vias can be hermetically sealed to the alumina, but the seal can be compromised by the combination of force and temperature used in these processes. Assuming this is a problem, a small modification to the process can resolve the issue. For instance, instead of aligning the vias and the gold balls to each other, the two array patterns can be offset by a predetermined distance. Each gold ball can still from a gold-to-gold bond with the thin films on the feedthrough but the vias will not be directly mechanically loaded due to the offset. An exemplary offset is shown in FIG. 25. In some cases, the laser dicing pattern can be adjusted so that each remaining thin film pad is also offset. This can help to maintain electrical conductivity from each electrode to its appropriate via in the array.

Array/Electrode Shapes

Figure 26:
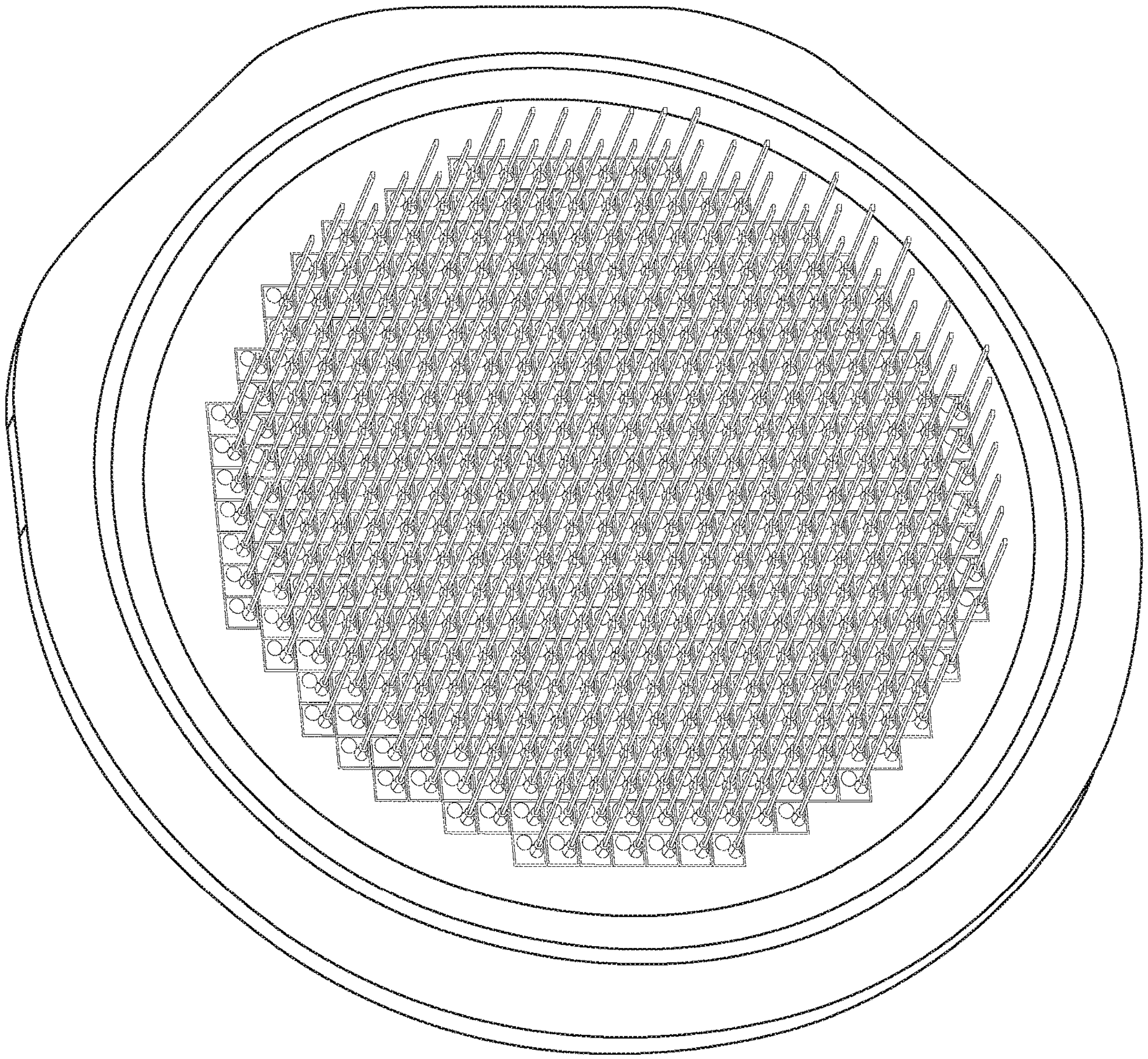
FIG. 26 schematically illustrates an example of a circular feedthrough with a circular array pattern, in accordance with some embodiments.

In some cases, the arrays formed using the presently disclosed methods may comprise a square array with regular spacing. Many variables in this array configuration can be altered to make the shape of the array irregular and/or non-square. Several alternative configurations include, for example, varying pitch in one or more directions, varying the pitch from one side to the other side, varying the height or size/shape of electrodes, making the array non-symmetric in one or two axes, making an array based on a hexagonal pattern, instead of a rectilinear pattern, or making the overall shape of the array non-square. An example of a circular feedthrough with a circular array pattern is shown in FIG. 26.

In some cases, the electrodes can be sharp, long, thin, and/or straight. All these parameters can be changed. In some embodiments, the electrodes can be sized and/or shaped to enhance the anchoring of the electrodes to a subject's tissue (e.g., brain tissue).

In any of the embodiments described herein, the array of electrodes can be processed to make the individual electrodes thinner and/or smoother. This can help to optimize the form factor of the electrodes for insertion into a subject's brain, while maintaining or enhancing the signal transmission and reception properties of the electrodes once inserted into the subject's brain.

In some cases, the electrodes can be processed using a multi-axis laser machining operation. In some cases, the multi-axis laser machining operation can comprise a 5-axis femtosecond laser machining operation. The laser machining operation may be performed using a femtosecond laser, which may comprise a laser (e.g., an infrared laser) that emits bursts of laser energy with a pulse duration in the femtosecond range.

In some cases, the electrodes can be processed using electropolishing. Electropolishing may comprise an electrochemical finishing process that can remove a thin layer of material from at least a portion of an electrode. Electropolishing can produce a shiny, smooth, ultra-clean surface finish for the electrodes in an array. In some cases, electropolishing can reduce a surface roughness of the electrodes by levelling micro-peaks and valleys, thereby improving the surface finish of the electrodes in the array.

Computer Systems

Figure 27:
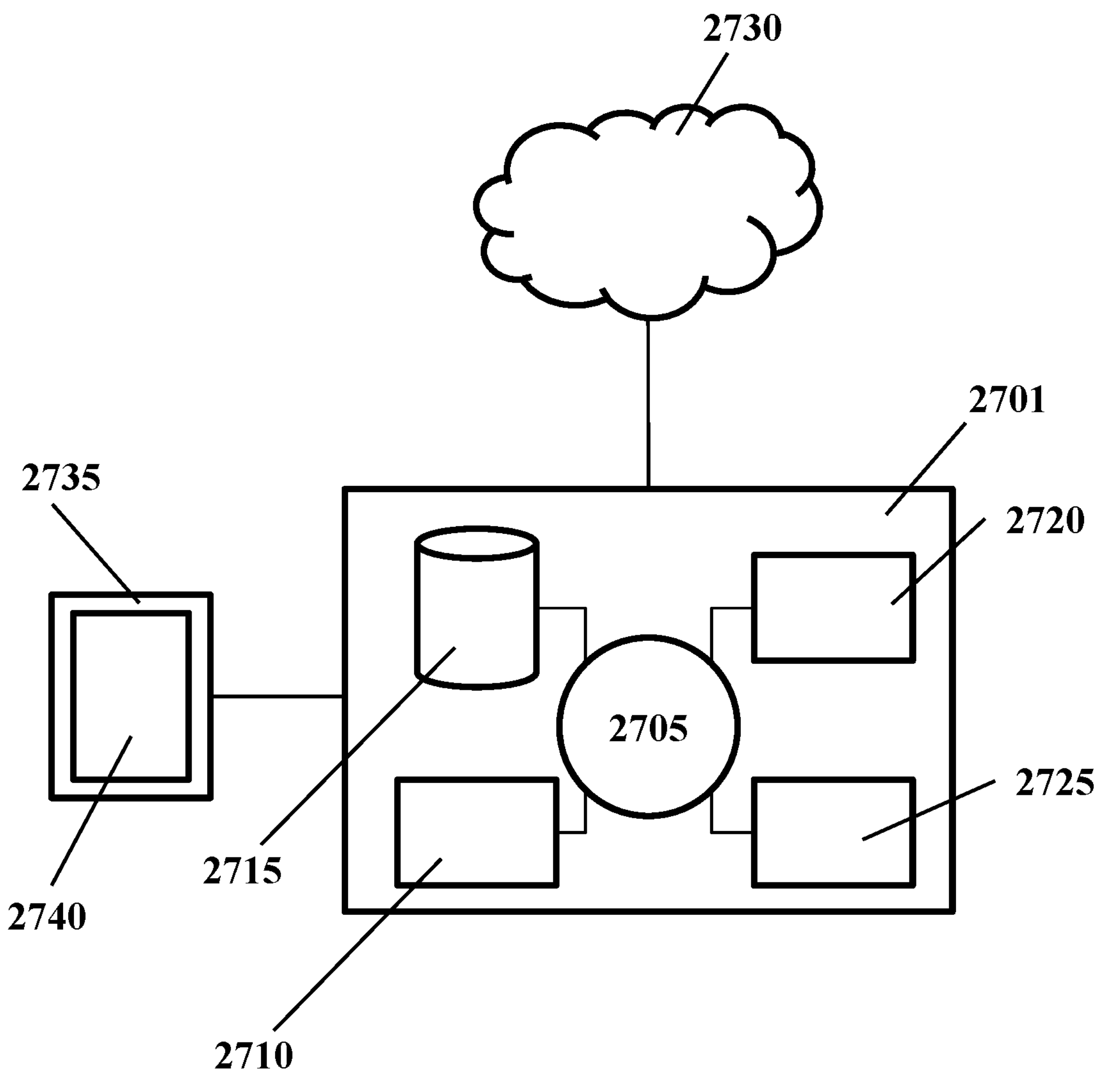
FIG. 27 schematically illustrates a computer system that is programmed or otherwise configured to implement methods provided herein.

In an aspect, the present disclosure provides computer systems that are programmed or otherwise configured to implement methods of the disclosure, e.g., any of the subject methods for manufacturing arrays. FIG. 27 shows a computer system 2701 that is programmed or otherwise configured to implement a method for manufacturing arrays. The computer system 2701 may be configured to, for example, control an operation of a machine or equipment to perform or facilitate (i) a processing of a source material to form one or more elongated features, (ii) a creation of a needle array from the elongated features, and/or (iii) a dicing of said needle array to form an array comprise a plurality of discrete electrodes. The computer system 2701 can be an electronic device of a user or a computer system that is remotely located with respect to the electronic device. The electronic device can be a mobile electronic device.

The computer system 2701 may include a central processing unit (CPU, also "processor" and "computer processor" herein) 2705, which can be a single core or multi core processor, or a plurality of processors for parallel processing. The computer system 2701 also includes memory or memory location 2710 (e.g., random-access memory, read-only memory, flash memory), electronic storage unit 2715 (e.g., hard disk), communication interface 2720 (e.g., network adapter) for communicating with one or more other systems, and peripheral devices 2725, such as cache, other memory, data storage and/or electronic display adapters. The memory 2710, storage unit 2715, interface 2720 and peripheral devices 2725 are in communication with the CPU 2705 through a communication bus (solid lines), such as a motherboard. The storage unit 2715 can be a data storage unit (or data repository) for storing data. The computer system 2701 can be operatively coupled to a computer network ("network") 2730 with the aid of the communication interface 2720. The network 2730 can be the Internet, an internet and/or extranet, or an intranet and/or extranet that is in communication with the Internet. The network 2730 in some cases is a telecommunication and/or data network. The network 2730 can include one or more computer servers, which can enable distributed computing, such as cloud computing. The network 2730, in some cases with the aid of the computer system 2701, can implement a peer-to-peer network, which may enable devices coupled to the computer system 2701 to behave as a client or a server.

The CPU 2705 can execute a sequence of machine-readable instructions, which can be embodied in a program or software. The instructions may be stored in a memory location, such as the memory 2710. The instructions can be directed to the CPU 2705, which can subsequently program or otherwise configure the CPU 2705 to implement methods of the present disclosure. Examples of operations performed by the CPU 2705 can include fetch, decode, execute, and writeback.

The CPU 2705 can be part of a circuit, such as an integrated circuit. One or more other components of the system 2701 can be included in the circuit. In some cases, the circuit is an application specific integrated circuit (ASIC).

The storage unit 2715 can store files, such as drivers, libraries and saved programs. The storage unit 2715 can store user data, e.g., user preferences and user programs. The computer system 2701 in some cases can include one or more additional data storage units that are located external to the computer system 2701 (e.g., on a remote server that is in communication with the computer system 2701 through an intranet or the Internet).

The computer system 2701 can communicate with one or more remote computer systems through the network 2730. For instance, the computer system 2701 can communicate with a remote computer system. Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system 2701 via the network 2730.

Methods as described herein can be implemented by way of machine (e.g., computer processor) executable code stored on an electronic storage location of the computer system 2701, such as, for example, on the memory 2710 or electronic storage unit 2715. The machine executable or machine readable code can be provided in the form of software. During use, the code can be executed by the processor 2705. In some cases, the code can be retrieved from the storage unit 2715 and stored on the memory 2710 for ready access by the processor 2705. In some situations, the electronic storage unit 2715 can be precluded, and machine-executable instructions are stored on memory 2710.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2701 can include or be in communication with an electronic display 2735 that comprises a user interface (UI) 2740. The portal may be provided through an application programming interface (API). A user or entity can also interact with various elements in the portal via the UI. Examples of UI's include, without limitation, a graphical user interface (GUI) and web-based user interface.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method, comprising:

(a) processing a source material using an additive or subtractive operation to form a plurality of elongated features;

(b) depositing one or more films on a surface portion of the plurality of elongated features;

(c) forming one or more electrical interconnections between (i) the plurality of elongated features and (ii) one or more active electronic components for processing one or more signals that are transmitted or received by or through the plurality of elongated features, wherein the one or more films are configured to modify a property of the surface portion of the plurality of elongated features to enable or facilitate the one or more electrical interconnections;

(d) creating a needle array from the plurality of elongated features; and (e) dicing said needle array to form an array comprising a plurality of discrete electrodes;

wherein the plurality of elongated features of (c) are in electrical communication with (i) each other and (ii) a worktable, via the one or more films prior to the dicing in (e).

2. The method of claim 1, wherein the additive or subtractive operation comprises electrical discharge machining (EDM).

3. The method of claim 2, wherein the electrical discharge machining comprises (i) wire EDM or (ii) sinker EDM.

4. The method of claim 1, wherein each discrete electrode of the array is electrically isolated from one or more other discrete electrodes of the array.

5. The method of claim 1, wherein the plurality of discrete electrodes are in communication with the one or more active electronic components to facilitate or enable signal transmission and processing.

6. The method of claim 1, wherein one or more discrete electrodes of the array are built or formed directly onto a hermetic feedthrough that is coupled to or integrated with a hermetic package comprising the one or more active electronic components.

7. The method of claim 1, wherein the one or more electrical interconnections comprise a ball bond or a stud bump.

8. The method of claim 1, wherein the one or more films comprise a semitransparent film.

9. The method of claim 1, wherein the one or more films comprise a layer of platinum and/or a layer of gold.

10. The method of claim 1, wherein the one or more electrical interconnections comprise one or more bonds formed by depositing a ball comprising a conductive material on the plurality of elongated features or the one or more films deposited thereon.

11. The method of claim 1, further comprising, prior to (c), providing a hermetic feedthrough comprising a plurality of vias for establishing or facilitating the one or more electrical interconnections between (i) the plurality of elongated features and (ii) the one or more active electronic components.

12. The method of claim 11, further comprising depositing one or more thin films on an outside surface of the hermetic feedthrough, wherein the one or more thin films are configured to modify a property of the outside surface of the hermetic feedthrough to enable or facilitate the one or more electrical interconnections.

13. The method of claim 11, wherein the one or more electrical interconnections are formed by bonding the plurality of vias to the plurality of elongated features, and wherein the plurality of vias and the plurality of elongated features are aligned with each other.

14. The method of claim 13, wherein the bonding of the plurality of vias and the plurality of elongated features comprises forming one or more gold-to-gold diffusion bonds.

15. The method of claim 14, further comprising heat treating the array to improve diffusion across the one or more gold-to-gold diffusion bonds and relieve residual stress.

16. The method of claim 1, wherein the needle array is formed by laser cutting, electrochemical machining, or mechanical dicing of the plurality of elongated features.

17. The method of claim 12, wherein the one or more electrical interconnections extend through one or more thin film stacks deposited on the outside surface of the hermetic feedthrough, wherein the one or more thin film stacks comprise the one or more thin films deposited on the outside surface of the hermetic feedthrough.

18. The method of claim 12, wherein (e) further comprises laser dicing (i) the one or more thin films deposited on the outside surface of the hermetic feedthrough and/or (ii) the one or more films deposited on the plurality of elongated features to form the plurality of discrete electrodes.

19. The method of claim 18, wherein the plurality of discrete electrodes are in electrical communication with the worktable and each other via the one or more films and the one or more thin films prior to said laser dicing of the one or more thin films or the one or more films.

20. The method of claim 18, wherein the plurality of discrete electrodes are (i) physically separate from each other, (ii) electrically isolated, and (iii) conductive through the hermetic feedthrough subsequent to said laser dicing of the one or more films.

21. The method of claim 1, wherein the source material comprises platinum-iridium, and wherein a film of the one or more films comprises titanium.

22. The method of claim 1, further comprising, prior to (c), providing a hermetic feedthrough between the plurality of elongated features and the one or more active electronic components, wherein a top surface of the hermetic feedthrough is in electrical communication with the plurality of elongated features, and wherein a bottom surface of the hermetic feedthrough is in electrical communication with (i) the one or more active electronic components, (ii) the worktable, or (iii) both.

23. The method of claim 11, wherein the one or more electrical interconnections are formed by bonding the plurality of vias to the plurality of elongated features, and wherein the plurality of vias and the plurality of elongated features are offset relative to each other.

* * * * *